(12) United States Patent
Askenasy

(10) Patent No.: US 7,138,144 B2
(45) Date of Patent: Nov. 21, 2006

(54) METHOD OF INDUCING IMMUNE TOLERANCE VIA BLOOD/LYMPH FLOW-RESTRICTED BONE MARROW TRANSPLANTATION

(76) Inventor: Nadir Askenasy, 7/14 Perlok Street, 69 367, Tel Aviv (IL)

( * ) Notice: Subject to any disclaimer, the term of this patent is extended or adjusted under 35 U.S.C. 154(b) by 571 days.

(21) Appl. No.: 10/237,033

(22) Filed: Sep. 9, 2002

(65) Prior Publication Data

US 2003/0064058 A1 Apr. 3, 2003

Related U.S. Application Data

(60) Provisional application No. 60/317,447, filed on Sep. 7, 2001.

(51) Int. Cl.
*A61K 35/26* (2006.01)
*A01N 47/40* (2006.01)
(52) U.S. Cl. ...................................... 424/577; 514/885
(58) Field of Classification Search ................ 424/577; 514/885
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |

OTHER PUBLICATIONS

Askenasy "Localized Bone Marrow Transplantation Leads to Skin Allograft Acceptance in Nonmyeloablated Recipients: Comparison of Intra-Bone Marrow and Isolated Limb Perfusion", Stem Cells, 20: 86-93, 2002.
Askenasy et al. "Cardiac Allograft Acceptance After Localized Bone Marrow Transplantation by Isolated Limb Perfusion in Nonmyeloablated Recipients", Stem Cells, 21: 200-207, 2003.
Baba et al. "Intra-Bone Marrow-Bone Marrow Transplantation Facilitates Hemopoietic Recovery Including Dendritic Cells", Immunobiology, 210: 33-42, 2005.
Bhatia et al. "Purification of Primitive Human Hematopoietic Cells Capable of Repopulating Immune-Deficient Mice", Proc. Natl. Acad. Sci. USA, 94: 5320-5325, 1997.
Bonnet et al. "Cytokine Treatment or Accessory Cells Are Required to Initiate Engraftment of Purified Primitive Human Hematopoietic Cells Transplanted at Limiting Doses Into NOD/SCID Mice", Bone Marrow Transplantation, 23: 203-209, 1999.
Burt et al. "Embryonic Stem Cells as An Alternative Marrow Donor Source: Engraftment Without Graft-Versus-Host Disease", Journal of Experimental Medicine, 199(7): 895-904, 2004.
Castello et al. "Intra-Bone Marrow Injection of Bone Marrow and Cord Blood Cells: An Alternative Way of Transplantation Associated With a Higher Seedings Efficiency", Experimental Hematology, 32: 782-787, 2004.
Chabner et al. "Direct Vascular Delivery of Primitive Hematopoietic Cells to Bone Marrow Improves Localization But Not Engraftment", Blood, 103(12): 4685-4686, 2004.
Esumi et al. "Successful Allogeneic Leg Transplantation in Rats in Conjunction With Intra-Bone Marrow Injection of Donor Bone Marrow Cells", Transplantation, 76(11): 1543-1548, 2003.
Fouillard et al. "Engraftment of Allogeneic Mesenchymal Stem Cells in the Bone Marrow of A Patient With Severe Idiopathic Aplastic Anemia Improves Stroma", Leukemia, 17: 474-476, 2003.
Gandy et al. "Tolerance of Allogeneic Heart Grafts in Mice Simultaneously Reconstituted With Purified Allogeneic Hematopoietic Stem Cells", Williams & Wilkins, 65(3): 295-304, 1998.
Gurevitch et al. "Reconstruction of Cartilage, Bone, and Hematopoietic Microenvironment With Demineralized Bone Matrix and Bone Marrow Cells", Stem Cells, 21: 588-597, 2003.
Hägglund et al. "Intraosseous Compared to Intravenous Infusion of Allogeneic Bone Marrow", Bone Marrow Transplantation, 21: 331-335, 1998.
Ikehara "New Strategies for BMT, Organ Transplantation, and Regeneration Therapy", Hematology, 8(2): 2003.
Ikehara "A New Concept of Stem Cell Disorders and Their New Therapy", Journal of Hematotherapy & Stem Cell Research, 12: 643-653, 2003.
Kaneda et al. "Long-Term Observation After Simultaneous Lung and Intra-Bone Marrow-Bone Marrow Transplantation", The Journal of Heart and Lung Transplantation, 24: 1415-1423, 2005.
Bahia Kerbauy et al. "Engraftment of Distinct Clonal MDS-Derived Hematopoietic Precursors in NOD/SCID-$\beta$2-Microglobulin-Deficient Mice After Intramedullary Transplantation of Hematopoietic and Stromal Cells", Blood, 104(7): 2202-2203, 2004.
Klicks et al. "Vascular Complications of Isolated Limb Perfusion", European Journal of Surgical Oncology, 24: 288-291, 1998.
Kushida et al. "Treatment of Intractable Autoimmune Diseases in MRL/Lpr Mice Using A New Strategy for Allogeneic Bone Marrow Transplantation", Blood, 95(5): 1862-1868, 2000.
Kushida et al. "Intra-Bone Marrow Injection of Allogeneic Bone Marrow Cells: A Powerful New Strategy for Treatment of Intractable Autoimmune Diseases in MRL/Lpr Mice", Blood, 97(10): 3192-3299, 2001.
Mazurier et al. "Rapid Myeloerythroid Repopulation After Intrafemoral Transplantation of NOD-SCID Mice Reveals A New Class of Human Stem Cells", Nature Medicine, 9(7): 959-963, 2003.

(Continued)

*Primary Examiner*—Christina Chan
*Assistant Examiner*—Belyavskyi

(57) ABSTRACT

A method of inducing tolerance to a transplant transplanted from a donor to a subject is disclosed. The method comprises (a) restricting outflow of a fluid from a portion of the circulatory system of the subject; and (b) administering a dose of bone marrow cells derived from the donor to a body part delimiting said portion of the circulatory system, prior to, concomitantly with or following transplantation of the transplant, thereby inducing tolerance to the transplant in the subject.

49 Claims, 5 Drawing Sheets

OTHER PUBLICATIONS

Nakamura et al. "Enhancement of Allogeneic Hematopoietic Stem Cell Engraftment and Prevention of GvHD by Intra-Bone Marrow Bone Marrow Transplantation Plus Donor Lymphocyte Infusion", Stem Cells, 22: 125-134, 2004.

Reisner et al. "Transplantation Tolerance Induced by 'Mega Dose' CD34+ Cell Transplants", Experimental Hematology, 28: 119-127, 2000.

Shizuru et al. "Purified Hematopoietic Stem Cell Grafts Induce Tolerance to Alloantigens and Can Mediate Positive and Negative T cell Selection", Proc. Natl. Acad. Sci. USA, 97(17): 9555-9560, 2000.

Slavin et al. "Induction of Specific Tissue Transplantation Tolerance Using Fractionated Total Lymphoid Irradiation in Adult Mice: Long-Term Survival of Allogeneic Bone Marrow and Skin Grafts", The Journal of Experimental Medicine, 146: 34-48, 1977.

Stam et al. "Systemic Toxicity and Cytokine/Acute Phase Protein Levels in Patients After Isolated Limb Perfusion With Tumor Necrosis Factor-α Complicated by High Leakage", Annals of Surgical Oncology, 7(4): 268-275, 2000.

Stein et al. "Critical Early Events in Hematopoietic Cell Seeding and Engraftment", Folia Histochemica et Cytobiologica, 43(4): 191-195, 2005.

Taira et al. "Treatment of Streptozotocin-Induced Diabetes Mellitus in Rats by Transplantation of Islet Cells From Two Major Histocompatibility Complex Disparate Rats in Combination With Intra Bone Marrow Injection of Allogeneic Bone Marrow Cells", Transplantation, 79(6): 680-687, 2005.

Tominaga et al. "Current Techniques of Hyperthermic Isolated Limb Perfusion for Malignant Melanoma", Surgery Today, 30: 339-342, 2000.

Uchida et al. "High Doses of Purified Stem Cells Cause Early Hematopoietic Recovery in Syngeneic and Allogeneic Hosts", The Journal of Clinical Investigation, 101(5): 961-966, 1998.

Van Hennik et al. "Seeding Efficiency of Primitive Human Hematopoietic Cells in Nonobese Diabetic/Severe Combined Immune Deficiency Mice: Implications for Stem Cell Frequency Assessment", Blood, 94(9): 3055-3061, 1999.

Verstegen et al. "Transplantation of Human Umbilical Cord Blood Cells in Macrophage-Depleted SCID Mice: Evidence for Accessory Cell Involvement in Expansion of Immature CD34+CD38- Cells", Blood, 91(6): 1966-1976, 1998.

Vrouenraets et al. "Toxicity and Morbidity of Isolated Limb Perfusion", Seminars in Surgical Oncology, 14: 224-231, 1998.

Wang et al. "SCID-Repopulating Cell Activity of Human Cord Blood-Derived CD34- Cells Assured by Intra-Bone Marrow Injection", 101: 2924-2931, 2003.

Wright et al. "Physiological Migration of Hematopoietic Stem and Progenitor Cells", Science, 294: 1933-1936, 2001.

Yahata et al. "A Highly Sensitive Strategy for SCID-Repopulating Cell Assay by Direct Injection of Primitive Human Hematopoietic Cells Into NOD/SCID Mice Bone Marrow", Blood, 101(8): 2905-2913, 2003.

Zhang et al. "Simultaneous Injection of Bone Marrow Cells and Stromal Cells Into Bone Marrow Accelerates Hematopoiesis In Vivo", Stem Cells, 22: 1256-1262, 2004.

Zhong et al. "Murine Hematopoietic Stem Cell Distribution and Proliferation in Ablated and Nonablated Bone Marrow Transplantation", Blood, 100(10): 3521-3526, 2002.

METHOD OF INDUCING IMMUNE TOLERANCE VIA BLOOD/LYMPH FLOW-RESTRICTED BONE MARROW TRANSPLANTATION

This application claims the benefit of priority from U.S. Provisional Patent Application No. 60/317,447 filed Sep. 7th, 2001.

FIELD AND BACKGROUND OF THE INVENTION

The present invention relates to methods of inducing immunological tolerance. More particularly, the present invention relates to the use of transplantation of allogeneic donor bone marrow cells (BMCs) to a restricted hematopoietic space of a sublethally conditioned host recipient to induce donor specific immunological tolerance in the host.

Transplantation of allogeneic donor cells, tissues or organs is central to the therapy of a large number of highly debilitating and/or lethal diseases, including many diseases for which such transplantation is the sole or highly preferred therapeutic option. For example, in the United States more than 19,000 transplants, half of the world total, are performed each year to treat many diseases collectively involving various tissues, including all major organs. The list of successfully transplanted cells, tissues and organs includes: kidney, heart, lung, liver, corneas, pancreas, pancreatic islets of Langerhans, intestines, brain tissue, liver, spleen, thymus, lymph nodes, bone marrow, skin, and bones. Combinations of tissue have also been transplanted, for example, bone marrow-solid organ transplants, heart-lung transplants, pancreas-kidney transplants, and pancreas-kidney-intestinal transplants.

Among the diseases which can be treated by bone marrow transplantation (BMT), are more than 20 otherwise fatal diseases that include the six or seven genetically different forms of severe combined immunodeficiency (SCID), various forms of congenital or genetically determined hematopoietic abnormalities, combinations of these two, certain anemias, osteopetrosis, a variety of high risk leukemias and several forms of severe life-threatening aplastic anemia. These diseases include severe combined immunodeficiency (SCID) autosomal recessive with and without B cells [no adenosine deaminase (ADA) deficiency]; SCID X-linked recessive without B cells; SCID autosomal recessive with ADA deficiency; Wiskott-Aldrich syndrome; Blackfan-Diamond syndrome; Fanconi anemia; severe neutrophil dysfunction; chronic granulomatous disease of childhood; severe (Kostman-type) agranulocytosis; immunodeficiency and neutropenia of cartilage-hair hypoplasia; infantile and late onset osteopetrosis; aplastic anemia-toxic chemical, idiopathic, immunological, and genetic (non-Fanconi); acute myeloid leukemia; chronic myeloid leukemia; Burkitt lymphoma, and recurrent acute lymphatic leukemia. Other diseases that have been treated recently with BMT include metabolic storage diseases such as Gaucher's disease, hemoglobinophaties such as thalassemia, and even some solid tumors such as neuroblastoma.

Autoimmune diseases have also come to be regarded as stem cell disorders in recent years and treatment of various autoimmune diseases by BMT is a focus of attention today (Ikehara S., 1998. Int J Mol Med. 1:5–16).

Transplantation of allogeneic cells, tissues and organs has the potential to treat the large numbers of patients who do not receive such therapy since, for example, in the United States more than 200,000 people suffer from kidney failure at any one time, and more 60,000 people die of liver failure yearly.

Due to the chronic shortage of compatible donors, each year more than 56,000 critically ill people in the United States are on waiting lists to receive an organ transplant that could prevent further death or disability.

However, transplantation of allogeneic cells, tissues or organs involves significant drawbacks for which no adequate solutions exist. Such drawbacks, including graft rejection, complications from immunosuppressive therapy and graft-versus-host disease, frequently occur, and are frequently highly debilitating or lethal.

All individuals express unique combinations of cell surface molecules, termed major histocompatibility antigens, which function to enable the immune system to distinguish self from non-self, and to thereby trigger immunological elimination of foreign tissues. Thus, transplantation therapies are burdened by the need to select transplant donors whose major histocompatibility antigens are as genetically close to those of the recipient as possible and by the mandatory requirement for life-long administration of potent immunosuppressive agents, such as cyclosporin, to combat graft rejection and graft-versus-host disease in transplant recipients.

Graft rejection may occur through a number of different mechanisms, with the time course of rejection being characteristic of the particular mechanism. Early rejection (hyperacute rejection) occurring within minutes or hours of transplantation, involves complement activation by components that are present at time of the transplant operation. Activation may occur via the classical pathway by preformed antibodies that are reactive with the "foreign" or non-self markers of the graft or via the alternative pathway in response to tissue damage in the graft as a result of, for example, ischemic damage to the organ during storage before transplantation. Acute rejection occurs days to weeks after transplantation, and is caused by sensitization of the host to the foreign tissue that makes up the graft. Once the host's immune system has identified the transplanted tissue as foreign, all the resources of the immune system are marshalled against the graft, including both specific (e.g., B-cell, and T-cell dependent) responses and non-specific (phagocytic, complement-dependent, etc.) responses. In cases where the graft recipient is immunosuppressed, chronic graft rejection, a T cell mediated process, will eventually occur within a number of years. In chronic graft rejection, the graft may survive long enough for tissue to undergo changes which ultimately affect survival of the graft. Such changes include hyperplasia, tissue hypertrophy, and endothelial cell damage leading to narrowing of the vascular lumen, potentially impairing the oxygen supply to the graft tissue. Rejected transplants must be surgically removed, and if the transplant is a life-sustaining organ such as a lung, liver, or heart, a patient may die before a replacement organ is found.

Although the standard use of immunosuppressive agents such as cyclosporin has greatly increased the short-term success rate, notably of transplants of solid organs such as kidney, and renders allogeneic transplantation practicable, such drugs display pronounced side-effects, such as dramatically increasing the risks of cardiovascular disease, potentially lethal opportunistic infections and malignancies. Furthermore, as described hereinabove chronic rejection sooner or later remains inevitable under current transplantation/immunosuppression regimens. Moreover, immunosuppressive drugs have not had a significant effect on long-term transplant survival. More than half of transplanted kidneys, the organ most often transplanted, are rejected within ten years, and the patient must receive another kidney transplant or start dialysis treatments, which are uncomfortable, expensive, and time-consuming.

Similarly to solid organ transplants, widespread clinical application of bone marrow transplantation (BMT) as a means of tolerance induction is restricted by the high morbidity and mortality rates associated with toxicity of conditioning, graft-versus-host disease and failure of engraftment (Armitage J O., 1994. New Engl J Med. 330:827).

Thus, because of the toxicity and incomplete response rate to conventional treatment of donor tissue rejection, alternative approaches are needed to induce immunological tolerance to allografts. Tolerance is the acquired lack of specific responsiveness to an antigen to which an immune response would normally occur. Typically, to induce tolerance, there must be an exposure to a tolerizing antigen, which results in the death or functional inactivation of certain lymphocytes. Complete tolerance is characterized by the lack of a detectable immune response to a repeat antigenic challenge, and partial tolerance is typified by a quantitative or qualitative reduction of an immune response.

One potentially promising strategy which has been employed to induce allogeneic donor specific immunological tolerance in a host without, or with reduced, life-long immunosuppressive drug regimens involves transplantation of donor bone marrow cells (BMCs) in the host. Establishment of donor specific hemopoietic chimerism in the host following such transplantation has been shown to correlate with tolerance of the host to subsequent donor derived grafts, including organ grafts (Ildstad S T. and Sachs D H., 1984. Nature 307:168; Ildstad S T. et al., 1985. J Exp Med. 162:231; Sharabi Y. and Sachs D., 1989. J Exp Med. 169:493; Markus P M. et al., 1993. Cell Transplant. 2:345). transplanted BMCs However, such an approach of inducing donor specific immunological tolerance in a host presents significant drawbacks. The lethal conditioning regimens, such as myoablative total body irradiation, required to ensure stable engraftment of allogeneic donor BMCs in the host are unacceptably dangerous, being often lethal or highly toxic; the efficiency of establishment of donor specific hemopoietic chimerism is highly inefficient; and such transplantation of allogeneic BMCs is associated with unacceptably high rates of graft-versus-host disease.

Various prior art approaches have been attempted for induction of donor specific immunological tolerance in a host via allogeneic donor BMC transplantation.

One approach has used high levels of whole body irradiation (1.5–3 Gy) to condition murine hosts prior to syngeneic donor BMC transplantation in attempt to facilitate donor specific hemopoietic chimerism. However, only about 50% of animals conditioned with 1.5 Gy WBI showed evidence for BMC engraftment (Tomita Y. et al., 1994. Blood 83:939).

Another approach has utilized whole body irradiation of at least 0.5–0.6 Gy to condition murine hosts prior to MHC-mismatched allogeneic donor BMC transplantation for induction of tolerance to subsequent donor type skin grafts. However, the level of donor chimerism achieved in these studies was less than 50% (Colson Y L. et al., 1995. J Immunol. 155:4179).

Yet another approach has utilized lethal whole body irradiation, to condition rat hosts prior to allogeneic donor BMC transplantation for induction of tolerance to subsequent donor type cardiac grafts. In this approach, however, only thirty-seven percent of animals displayed stable hemopoietic chimerism (Markus P M. et al., 1993. Cell Transplant. 2:345).

Still another approach has employed supralethal conditioning of rat hosts prior to allogeneic+ syngeneic donor T cell depleted BMC transplantation for induction of tolerance to subsequent donor type skin or cardiac grafts (Colson Y. et al., 1995. Transplantation 60:971).

Yet still another approach has used 0.3 Gy whole body irradiation and administration of anti-lymphocyte globulin and cyclophosphamide to condition murine hosts prior to allogeneic donor BMC transplantation for induction of tolerance to subsequent donor type skin grafts (Colson Y. et al., 1996. J Immunol. 157:2820).

A further approach has utilized 3 Gy whole body irradiation and administration of anti-T cell monoclonal antibodies to condition murine hosts prior to allogeneic donor BMC transplantation for induction of tolerance to subsequent donor type skin grafts (Tomita Y. et al., 1996. Transplantation 61:469).

Yet a further approach has employed administration of CTLA4-Ig to condition murine hosts prior to allogeneic donor BMC transplantation for induction of tolerance to subsequent donor type skin or cardiac grafts (Pearson T C. et al., 1996. Transplantation 61:997). Such inhibition of costimulatory pathways, however did not induce optimal long-term tolerance to the secondary organ grafts, and the immune suppression was not donor specific.

Still a further approach has employed anti-CD4 and anti-CD8 mAbs, 300-rad whole body irradiation, and 700-rad thymic irradiation to condition murine hosts prior to allogeneic donor BMC transplantation for induction of tolerance to subsequent donor type skin grafts (Sharabi Y. and Sachs D., 1989. J Exp Med. 169:493).

Yet still a further approach has utilized 5.5 Gy whole body irradiation to condition murine hosts prior to transplantation of allogeneic donor BMCs via portal vein injection for treatment of autoimmune disease (Kushida T. et al., 2000. Blood 95:1862).

An additional approach has employed 5.5 Gy whole body irradiation to condition murine hosts prior to transplantation of allogeneic donor BMCs via intra-bone marrow (IB) injection for treatment of autoimmune disease (Kushida T. et al., 2001. Blood 97:3292).

Yet an additional approach has used intra-osseous injection of allogeneic bone marrow in patients receiving marrow transplants from HLA-identical or one antigen-mismatched related donors (Hagglund H. et al., 1998. Bone Marrow Transplantation 21:331). In these trials, however, haematopoietic recovery was not improved relative to intravenous bone marrow administration.

Still an additional approach has utilized 6.5 Gy whole body irradiation to condition murine hosts prior to transplantation of a megadose of allogeneic donor BMCs for induction of donor specific hemopoietic chimerism (Bachar-Lustig B et al., 1995. Nat Med 1:1268).

Yet still an additional approach has employed transplantation of a megadose of allogeneic donor stem cells via intravenous injection for induction of donor specific hemopoietic chimerism in mice (Gandy K L and Weissman I L. 1998. Transplantation 65:295).

Another approach has used 0.5 Gy whole body irradiation, tacrolimus and anti lymphocyte serum to condition murine hosts prior to transplantation of a megadose of allogeneic donor BMCs for induction of tolerance to subsequent donor type cardiac grafts (Sykes M. et al., 1997. Nat Med. 3:783).

Yet another approach has used transplantation of megadoses of c-Kit+Thy-1.1(lo)Lin−/loSca-1+allogeneic donor BMCs for induction of donor specific hemopoietic chimerism in mice (Uchida N. et al., 1998. J Clin Invest. 101:961).

Yet another approach has utilized transplantation of megadoses of allogeneic donor Scal+Lin− BMCs in attempts to induce tolerance to subsequent donor type skin grafts (Reisner Y. and Martelli M F., 2000. Exp Hematol. 28:119).

However, all of the aforementioned approaches suffer from significant disadvantages. All prior art approaches have either employed BMC megadoses in mice which cannot be practically achieved in humans; have not shown efficient engraftment of transplanted cells, tissues or organs; have not shown satisfactory long-term survival of BMC and/or secondary organ grafts; have employed harmful whole body irradiation; have employed lethal or supralethal conditioning regimens; have employed toxic drugs for conditioning; have employed inefficient intravenous injection for delivery of BMCs; have not addressed issues of donor specific hemopoietic chimerism and/or tolerance to secondary donor organ grafts; have not demonstrated the capacity to induce immunological tolerance to different donor type secondary organ grafts; have not demonstrated the capacity to induce tolerance to a solid graft administered simultaneously with a tolerogenic dose of BMCs; and/or have resulted in unacceptable rates of graft-versus-host disease.

Thus, all prior art approaches have failed to provide an adequate solution for safely, effectively, and flexibly inducing allogeneic donor specific immunological tolerance via administration of donor-derived BMCs.

There is thus a widely recognized need for, and it would be highly advantageous to have, a method of inducing immunological tolerance devoid of the above limitation.

SUMMARY OF THE INVENTION

According to one aspect of the present invention there is provided a method of inducing tolerance to a transplant transplanted from a donor to a subject, the method comprising: (a) restricting outflow of a fluid from a portion of the circulatory system of the subject; and (b) administering a dose of bone marrow cells derived from the donor to a body part delimiting the portion of the circulatory system, prior to, concomitantly with or following transplantation of the transplant, thereby inducing tolerance to the transplant in the subject.

According to further features in preferred embodiments of the invention described below, step (a) is effected prior to step (b).

According to still further features in preferred embodiments, the method of inducing tolerance further comprises the step of conditioning the subject under sublethal, lethal or supralethal conditions prior to step (b).

According to still further features in preferred embodiments, the conditioning is effected by administering a dose of irradiation essentially exclusively to the body part or to a portion of the body part, the dose of irradiation selected capable of inducing myeloreduction or myeloablation essentially exclusively in the body part or the portion of the body part.

According to still further features in preferred embodiments, the conditioning is effected by administering a dose of a myeloablative agent to the subject.

According to still further features in preferred embodiments, the myeloablative agent is busulfan.

According to still further features in preferred embodiments, the dose of busulfan is less than or equal to a number of milligrams per kilogram body weight selected from a range of about 35 milligrams per kilogram body weight to about 145 milligrams per kilogram body weight.

According to still further features in preferred embodiments, the restricting outflow of a fluid is effected using a method selected from the group consisting of applying at least one tourniquet to at least one margin of the body part, anastomosing the portion of the circulatory system to a perfusion apparatus so as to form an isolated circulatory system therewith, and ligating at least one vessel conducting the outflow of fluid.

According to still further features in preferred embodiments, the method of inducing tolerance further comprises the step of restricting inflow of the fluid to the portion of the circulatory system.

According to still further features in preferred embodiments, the restricting inflow of the fluid is effected prior to step (b).

According to still further features in preferred embodiments, the restricting inflow of a fluid is effected using a method selected from the group consisting of applying at least one tourniquet to at least one margin of the body part, anastomosing the portion of the circulatory system to a perfusion apparatus so as to form an isolated circulatory system therewith, and ligating at least one vessel conducting the inflow of fluid.

According to still further features in preferred embodiments, the administering a dose of bone marrow cells is effected by administering the dose of bone marrow cells to the portion of the circulatory system.

According to still further features in preferred embodiments, the fluid is blood or lymph.

According to still further features in preferred embodiments, the subject is human or murine.

According to still further features in preferred embodiments, the dose of bone marrow cells is less than or equal to a number of cells per kilogram body weight selected from a range of about forty million cells per kilogram body weight to about 2 billion cells per kilogram body weight.

According to still further features in preferred embodiments, the dose of bone marrow cells is a dose of whole bone marrow cells or a dose of T-cell depleted bone marrow cells.

According to still further features in preferred embodiments, the dose of bone marrow cells is a dose of erythrocyte depleted bone marrow cells.

According to still further features in preferred embodiments, the dose of bone marrow cells is a dose of nucleated bone marrow cells.

According to still further features in preferred embodiments, the donor and the subject are allogeneic.

According to still further features in preferred embodiments, the body part contains a bone tissue.

According to still further features in preferred embodiments, the bone tissue is a bone marrow tissue.

According to still further features in preferred embodiments, the body part is a limb or a portion thereof.

According to still further features in preferred embodiments, the limb is a leg.

According to still further features in preferred embodiments, the transplant is selected from the group consisting of an organ transplant, a tissue transplant and a cell transplant.

According to still further features in preferred embodiments, the organ transplant is a cardiac transplant.

According to still further features in preferred embodiments, the tissue transplant is a skin transplant.

According to still further features in preferred embodiments, the cell transplant is a bone marrow cell transplant.

According to still further features in preferred embodiments, the cell transplant is the dose of bone marrow cells.

According to another aspect of the present invention there is provided a method of transplanting a transplant from a donor to a subject, the method comprising: (a) restricting outflow of a fluid from a portion of the circulatory system of the subject; (b) administering a dose of bone marrow cells derived from the donor to a body part delimiting the portion of the circulatory system; and (c) transplanting the transplant from the donor to the subject prior to, concomitantly with or following step (b).

According to further features in preferred embodiments of the invention described below, step (a) is effected prior to step (b).

According to still further features in preferred embodiments, the method of transplanting a transplant further comprises the step of conditioning the subject under sublethal, lethal or supralethal conditions prior to step (b).

According to still further features in preferred embodiments, the conditioning is effected by administering a dose of irradiation essentially exclusively to the body part or to a portion of the body part, the dose of irradiation selected capable of inducing myeloreduction or myeloablation essentially exclusively in the body part or the portion of the body part.

According to still further features in preferred embodiments, the conditioning is effected by administering a dose of a myeloablative agent to the subject.

According to still further features in preferred embodiments, the myeloablative agent is busulfan.

According to still further features in preferred embodiments, the dose of busulfan is less than or equal to a number of milligrams per kilogram body weight selected from a range of about 35 milligrams per kilogram body weight to about 145 milligrams per kilogram body weight.

According to still further features in preferred embodiments, the restricting outflow of a fluid is effected using a method selected from the group consisting of applying at least one tourniquet to at least one margin of the body part, adjoining the portion of the circulatory system to a perfusion apparatus so as to form an isolated circulatory system therewith, and ligating at least one vessel conducting the outflow of fluid.

According to still further features in preferred embodiments, the method of transplanting a transplant further comprises the step of restricting inflow of the fluid to the portion of the circulatory system.

According to still further features in preferred embodiments, the restricting inflow of the fluid is effected prior to step (b).

According to still further features in preferred embodiments, the restricting inflow of a fluid is effected using a method selected from the group consisting of applying at least one tourniquet to at least one margin of the body part, anastomosing the portion of the circulatory system to a perfusion apparatus so as to form an isolated circulatory system therewith, and ligating at least one vessel conducting the inflow of fluid.

According to still further features in preferred embodiments, the administering a dose of bone marrow cells is effected by administering the dose of bone marrow cells to the portion of the circulatory system.

According to still further features in preferred embodiments, the fluid is blood or lymph.

According to still further features in preferred embodiments, the subject is human or murine.

According to still further features in preferred embodiments, the dose of bone marrow cells is less than or equal to a number of cells per kilogram body weight selected from a range of about forty million cells per kilogram body weight to about 2 billion cells per kilogram body weight.

According to still further features in preferred embodiments, the dose of bone marrow cells is a dose of whole bone marrow cells or a dose of T-cell depleted bone marrow cells.

According to still further features in preferred embodiments, the dose of bone marrow cells is a dose of erythrocyte depleted bone marrow cells.

According to still further features in preferred embodiments, the dose of bone marrow cells is a dose of nucleated bone marrow cells.

According to still further features in preferred embodiments, the donor and the subject are allogeneic.

According to still further features in preferred embodiments, the body part contains a bone tissue.

According to still further features in preferred embodiments, the bone tissue is a bone marrow tissue.

According to still further features in preferred embodiments, the body part is a limb or a portion thereof.

According to still further features in preferred embodiments, the limb is a leg.

According to still further features in preferred embodiments, the transplant is selected from the group consisting of an organ transplant, a tissue transplant and a cell transplant.

According to still further features in preferred embodiments, the organ transplant is a cardiac transplant.

According to still further features in preferred embodiments, the tissue transplant is a skin transplant.

According to still further features in preferred embodiments, the cell transplant is a bone marrow cell transplant.

According to still further features in preferred embodiments, the cell transplant is the dose of bone marrow cells.

According to yet another aspect of the present invention there is provided a method of administering a dose of cells exclusively to a portion of the circulatory system of a subject, the method comprising: (a) restricting outflow of a fluid from a portion of the circulatory system of the subject; and (b) administering the dose of cells to a body part delimiting the portion of the circulatory system.

According to further features in preferred embodiments of the invention described below, the method of administering a dose of cells further comprises the step of conditioning the subject under sublethal, lethal or supralethal conditions prior to step (b).

According to still further features in preferred embodiments, the conditioning is effected by administering a dose of irradiation essentially exclusively to the body part or to a portion of the body part, the dose of irradiation selected capable of inducing myeloreduction or myeloablation essentially exclusively in the body part or in the portion of the body part.

According to still further features in preferred embodiments, the conditioning is effected by administering a dose of a myeloablative agent to the subject.

According to still further features in preferred embodiments, the myeloablative agent is busulfan.

According to still further features in preferred embodiments, the dose of busulfan is less than or equal to a number of milligrams per kilogram body weight selected from a range of about 35 milligrams per kilogram body weight to about 145 milligrams per kilogram body weight.

According to still further features in preferred embodiments, the restricting outflow of a fluid is effected using a method selected from the group consisting of applying at least one tourniquet to at least one margin of the body part, adjoining the portion of the circulatory system to a perfusion apparatus so as to form an isolated circulatory system therewith, and ligating at least one vessel conducting the outflow of fluid.

According to still further features in preferred embodiments, the method of administering a dose of cells further comprises the step of restricting inflow of the fluid to the portion of the circulatory system.

According to still further features in preferred embodiments, the restricting inflow of the fluid is effected prior to step (b).

According to still further features in preferred embodiments, the restricting inflow of a fluid is effected using a method selected from the group consisting of applying at least one tourniquet to at least one margin of the body part, anastomosing the portion of the circulatory system to a perfusion apparatus so as to form an isolated circulatory system therewith, and ligating at least one vessel conducting the inflow of fluid.

According to still further features in preferred embodiments, the administering the dose of cells is effected by administering the dose of cells to the portion of the circulatory system.

According to still further features in preferred embodiments, the fluid is blood or lymph.

According to still further features in preferred embodiments, the subject is human or murine.

According to still further features in preferred embodiments, the dose of cells is less than or equal to a number of cells per kilogram body weight selected from a range of about forty million cells per kilogram body weight to about 2 billion cells per kilogram body weight.

According to still further features in preferred embodiments, the dose of cells is a dose of bone marrow cells.

According to still further features in preferred embodiments, the dose of bone marrow cells is a dose of whole bone marrow cells or a dose of T-cell depleted bone marrow cells.

According to still further features in preferred embodiments, the dose of bone marrow cells is a dose of erythrocyte depleted bone marrow cells.

According to still further features in preferred embodiments, the dose of bone marrow cells is a dose of nucleated bone marrow cells.

According to still further features in preferred embodiments, the dose of cells and the subject are allogeneic.

According to still further features in preferred embodiments, the body part contains a bone tissue.

According to still further features in preferred embodiments, the bone tissue is a bone marrow tissue.

According to still further features in preferred embodiments, the body part is a limb or a portion thereof.

According to still further features in preferred embodiments, the limb is a leg.

The present invention successfully addresses the shortcomings of the presently known configurations by providing a method of inducing long-term tolerance to allogeneic transplants in recipients via bone marrow cell transplantation, which method characterized by: requiring reduced doses of bone marrow cells; not requiring myeloablative conditioning or life-long immunosuppressive regimens; and preventing graft-versus-host disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3a is data plot depicting survival of Balb/c mice treated with busulfan only at doses of 35, 70, 110, and 145 micrograms/g body weight (Bus 35, Bus 70, Bus 110, and Bus 145, respectively). FIG. 3b is a data plot depicting the percentage of donor peripheral blood lymphocytes (PBLs) in Balb/c recipients conditioned with increasing doses of busulfan, four weeks following administration of $10^7$ whole BMCs from B10 donors. FIG. 3c is a data plot depicting the percentage of donor PBLs in peripheral blood of recipients conditioned with 70 micrograms busulfan/g body weight four weeks following administration of $1 \times 10^6$, $5 \times 10^6$, $1 \times 10^7$, and $5 \times 10^7$ whole BMCs. FIG. 3d is a histogram depicting the percentage of donor PBLs in peripheral blood of recipients following administration of $10^7$ whole or T cell-depleted (TCD) BMCs in recipients conditioned with 70 micrograms busulfan/g body weight.

FIG. 5a depicts the percentage of donor $H2^b$ cells in the peripheral blood of recipients and FIG. 5b depicts the percentage of CD3-positive (T cells) and B220-positive (B cells) in the $H2^b$ donor fraction. Error bars represent standard deviations. *$p<0.05$ versus IV-BMT, #$p<0.05$ versus 3 weeks.

DESCRIPTION OF THE PREFERRED EMBODIMENTS

Figure 1A:
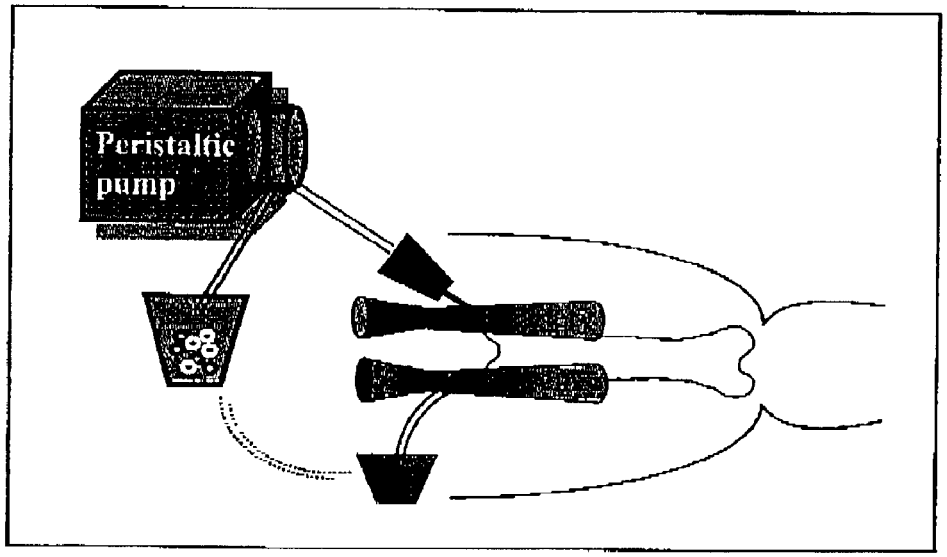
FIGS. 1a–b are schematic diagrams depicting the procedure for isolated limb BMT (IL-BMT) (FIG. 1a) and intra-bone marrow BMT (IB-BMT) (FIG. 1b) of bone marrow cells. For IL administration, the femoral artery and vein of the isolated limb were occluded and cannulated with 24 G catheters. The limb was perfused with Krebs-Henseleit physiological solution (KH), KH with donor cells and KH at a rate of 0.2 ml/minute, for 5, 10 and 10 minutes respectively. After perfusion blood flow in the femoral artery was restored and the femoral vein remained occluded. For IB administration, cells suspended in PBS were infused with a peristaltic minipump into the bone marrow through a needle inserted into the distal femoral epiphysis. Infusion rate was monitored with a pressure transducer and the medium was diverted into a reservoir when it reached a threshold of 8 or 20 mm Hg.

The present invention is of methods of administering a dose of cells to a subject, methods of inducing tolerance to a transplant transplanted from a donor to a subject, and of methods of transplanting a transplant from a donor to a subject. Specifically, the present invention can be used to administer a dose of cells to a body part of a subject and to inhibit dissemination of the dose of administered cells from the body part. In particular, the present invention can be used to induce tolerance to any donor-derived allogeneic transplant in a non-lethally conditioned subject by administration of a dose of donor bone marrow cells, including tolerance to the administered bone marrow cells themselves. The present invention can also be used to induce tolerance to an allogeneic donor-derived transplant transplanted simultaneously with the dose of donor-derived bone marrow cells, and to reconstitute hemopoiesis in a myeloablated subject with reduced risk of graft-versus-host disease.

As such, the method can be used to treat the very broad variety of highly debilitating or lethal illnesses susceptible to treatment via transplantation of a donor-derived transplant, which method being more efficient, safe, and versatile relative to all prior art methods.

The principles and operation of the present invention may be better understood with reference to the drawings and accompanying descriptions.

Before explaining at least one embodiment of the invention in detail, it is to be understood that the invention is not limited in its application to the details of construction and the arrangement of the components exemplified in the Examples. The invention is capable of other embodiments or of being practiced or carried out in various ways. Also, it is to be understood that the phraseology and terminology employed herein is for the purpose of description and should not be regarded as limiting.

Various methods of inducing tolerance to a transplant by administration of a tolerogenic dose of bone marrow cells have been described by the prior art.

Such methods have employed various combinations of lethal or supralethal conditioning, such as methods involving myeloablative whole body irradiation or drug induced myeloablation, methods involving systemic administration of insufficient doses of bone marrow cells, and methods involving administration of T cell depleted bone marrow cells.

However, methods employing lethal or supralethal conditioning have unacceptably harmful side-effects; methods involving systemic administration of insufficient doses of bone marrow cells result in unacceptably high rates of graft rejection, preclude simultaneous administration of a tolerogenic dose of bone marrow cells and transplantation of a tissue or organ transplant to induce tolerance to the transplant, and result in suboptimal homing of administered bone marrow cells to bone marrow tissue; and methods involving T cell depletion result in unacceptably low rates of engraftment, and transplantation of whole bone marrow cells result in unacceptably high rates of graft-versus-host disease.

Thus, all prior art approaches employing administration of a dose of bone marrow cells to induce tolerance to a transplant have failed to provide solutions for inducing tolerance to a donor-derived graft with optimal safety, effectiveness and versatility.

While reducing the present invention to practice it was unexpectedly uncovered that administering a dose of bone marrow cells to a flow-restricted portion of the circulatory system of a subject, which portion being delimited by a body part containing a bone marrow tissue, could be used to: induce greater homing or retention of administered bone marrow cells to bone marrow tissue relative to prior art methods; efficiently induce long-term tolerance to allogeneic cell, tissue or organ transplants in conjunction with sublethal conditioning only, in sharp contrast to all prior art methods; uniquely, relative to all prior art methods, induce tolerance in non-myeloablated subjects to an organ transplant transplanted simultaneously with a tolerogenic dose of bone marrow cells; and induce donor specific tolerance with reduced risk of graft-versus-host disease relative to prior art methods.

Thus, according to one aspect of the present invention there is provided a method of administering a dose of cells exclusively to a portion of the circulatory system of a subject.

As described in detail in the following Examples section, the method is effected by restricting outflow of a fluid from, and preferably also inflow of the fluid to, the portion of the circulatory system of the subject, and administering the dose of cells to a body part delimiting the portion of the circulatory system.

According to this aspect of the present invention, the dose of cells may be administered in various ways, depending on the context and purpose of the application.

For example, the dose of cells may be administered via intra-bone perfusion, or it may be administered to the portion of the circulatory system.

Preferably, the dose of cells is administered to the portion of the circulatory system, for example, essentially as described in the following Examples section, via injection into a blood vessel of the portion of the circulatory system.

Since the circulatory system conducts the flow of fluids such as blood and lymph which mediate systemic dissemination of cells administered to the circulatory system, the method according to this aspect of the present invention is advantageously effected by restricting the flow of lymph, more preferably of blood, and most preferably of both lymph and blood.

Depending on the application and purpose, various methods can be used for restricting fluid flow, including, but not limited to, applying at least one tourniquet to at least one margin of the body part, anastomosing the portion of the circulatory system to a perfusion apparatus so as to form an isolated circulatory system therewith, or ligating at least one vessel conducting the inflow or outflow of the fluid.

Regardless of the method employed to restrict fluid flow, the method is employed in such a way as to result in optimal retention of administered cells in the body part.

Due to the ease of tourniquet application to a body part such as a limb, or a portion thereof, fluid flow restriction is preferably effected by applying at least one tourniquet to at least one margin of the body part. Ample guidance regarding suitable types of tourniquets and methods of their use can be obtained from the literature of the art (see, for example: Wakai A. et al., J 2001. Am Acad Orthop Surg. 9(5):345–51; U.S. patent application Ser. No. US20010029389A1; Eur. Pat. No. EP0552148B1).

Ample guidance for safely and effectively anastomosing a perfusion apparatus, advantageously a continuous perfusion apparatus, to a portion of the circulatory system so as to form an isolated circulatory system therewith can be found in the following Examples section and in the literature of the art (for example, refer to: Schaadt J. et al., 2002. J Extra Corpor Technol. 34(2):130–43; Schraffordt Koops H. et al., 1975. Arch Chir Neerl. 27:237; Vrouenraets B C. et al, 1998. Semin Surg Oncol. 14:224; Tominaga R. et al., 2000. Surg Today 30:339).

Ligation of a vessel, such as a blood vessel or a lymphatic duct, so as to restrict fluid flow therethrough may be advantageously effected using surgical ligation clips. Ample guidance regarding selection of suitable surgical ligation clips and methods of their use to restrict flow in vessels can be obtained from the literature of the art (see, for example: U.S. Pat. No. 6,290,575).

One of ordinary skill in the art, such as for example, a vascular surgeon or a physician, would possess the expertise required for application of any of the above-described methods of restricting fluid flow to or from a portion of the circulatory system.

Tourniquet application to a limb to restrict fluid flow thereto or therefrom may be effected by applying a tourniquet to the limb at a level corresponding to the distal margin of the body part, more preferably at a level corresponding to the proximal margin of the body part, and most preferably at both a level corresponding to the distal margin of the body part and a level corresponding to the proximal margin of the body part.

Application of a tourniquet to the limb at a level corresponding to the proximal margin of the body part may be advantageous relative to application to of a tourniquet to the limb at a level corresponding to the distal margin of the body part. Tourniquet application at the proximal margin restricts fluid flow between the part of the circulatory system proximal to the portion of the circulatory system whose volume is significantly greater than the part of the circulatory system distal to the portion of the circulatory system. Thus, tourniquet application at the proximal margin can be used to obtain greater retention of administered bone marrow cells in the body part relative to tourniquet application at the distal margin. As described in the Examples section below, tourniquet application at the proximal margin of the body part can be used to obtain optimal retention of administered bone marrow cells in the bone tissue.

Tourniquet application at both proximal and distal margins of the body part is highly preferred since this enables optimal retention of administered bone marrow cells in the body part.

Application of a tourniquet at the proximal margin of the leg can be advantageously used to effectively promote retention of cells administered intravenously to the leg, as described in the Examples section below.

Following fluid flow restriction, the dose of cells is administered to the body part.

Following administration of the dose of cells, fluid flow in the portion of the circulatory system is restored following a suitable time interval, for example as described in the following Examples section.

The method can be used to administer a dose of essentially any type of cells exclusively to the portion of the circulatory system. The capacity of the method to optimally promote retention of administered cells in the portion of the circulatory system, and thereby in the body part delimiting the portion of the circulatory system, can be advantageously employed, for example, in essentially any therapeutic application benefiting from optimal localization and retention of administered cells in a body part, as further described hereinbelow.

Examples of cell types which can be advantageously administered exclusively to a body part include bone marrow cells, or any type of immune cells, such as antigen-presenting cells, splenocytes, and dendritic cells.

Preferably, the method is used to administer a dose of bone marrow cells to the body part.

Preferably, the dose of bone marrow cells comprises hematopoietic stem cells and/or hematopoietic progenitor cells. Inclusion of such cells in the dose of bone marrow cells may facilitate tolerance induction, as described in detail above and as further described hereinbelow.

As shown in FIGS. 3b–d, 4a–d and 5a–b of the following Examples section, administration of a dose of bone marrow cells according to the this aspect of the method of the present invention can be used to induce donor specific tolerance in the subject.

Thus, according to another aspect of the present invention, there is provided a method of inducing tolerance to a transplant transplanted from a donor to a subject.

As described in detail in the following Examples section, the method is effected by administering a dose of bone marrow cells derived from a donor to the body part, prior to, concomitantly with or following transplantation of the transplant.

The method of the present invention can be used to induce tolerance to any allogeneic transplant in any transplantation context.

For example, the method of the present invention can be advantageously used to induce tolerance to a transplant such as, but not limited to, an organ transplant, a tissue transplant, a cell transplant, and an appendage transplant.

As used herein, the phrase "organ transplant" refers to a transplant of a whole organ, or a transplant of any portion of an organ.

Preferably, the method of the present invention is employed to induce tolerance to a transplant transplanted from an allogeneic human donor to a human subject.

Examples of organ transplants include, but are not limited to, kidney, heart, liver, lung, and pancreas.

As shown in the following Examples section, the method can be used to induce tolerance to a cardiac allograft.

By virtue of enabling the complete replacement of an organ or portion thereof, the method of the present invention can be used, for example, to treat essentially any disease, disorder or condition associated with pathogenesis, degeneration or deficiency of the organ or portion thereof.

Examples of appendage transplants include, but are not limited to, arms, legs, hands, feet, fingers, toes and portions thereof.

Examples of tissue transplants include, but are not limited to, dermal, pancreatic islets and nerve tissues.

As shown in the following Examples section, the method can be used to induce tolerance to a skin allograft.

Examples of cell transplants include, but are not limited to, bone marrow cells, embryonic stem cells, pancreatic islet β cells, and hematopoietic stem cells.

As previously described hereinabove and as shown in the following Examples section, the method can be used to induce tolerance to a bone marrow cell allograft, in particular to a bone marrow cell allograft comprising hematopoietic stem cells, as shown in FIGS. 4a–d of the following Examples section.

Transplants of bone marrow cells; or of hematopoietic stem cells derived from bone marrow, mobilized peripheral blood (by, for example, leukapheresis), fetal liver, yolk sac or cord blood; can be employed, for example, to treat hematological deficiencies, including those arising as a consequence of medical treatment. Such hematological deficiencies can be, but are not limited to, severe combined immunodeficiency (SCID) syndromes (such as, for example adenosine deaminase (ADA) deficiency and X-linked SCID (XSCID), osteopetrosis, aplastic anemia, Gaucher's disease, thalassemia and other congenital or genetically-determined hematopoietic abnormalities. Hematological malignancies can be treated, but are not limited to, leukemias, such as acute lymphoblastic leukemia (ALL), acute nonlymphoblastic leukemia (ANLL), acute myelocytic leukemia (AML) or chronic myelocytic leukemia (CML), and malignancies such as melanoma.

Figure 5A:
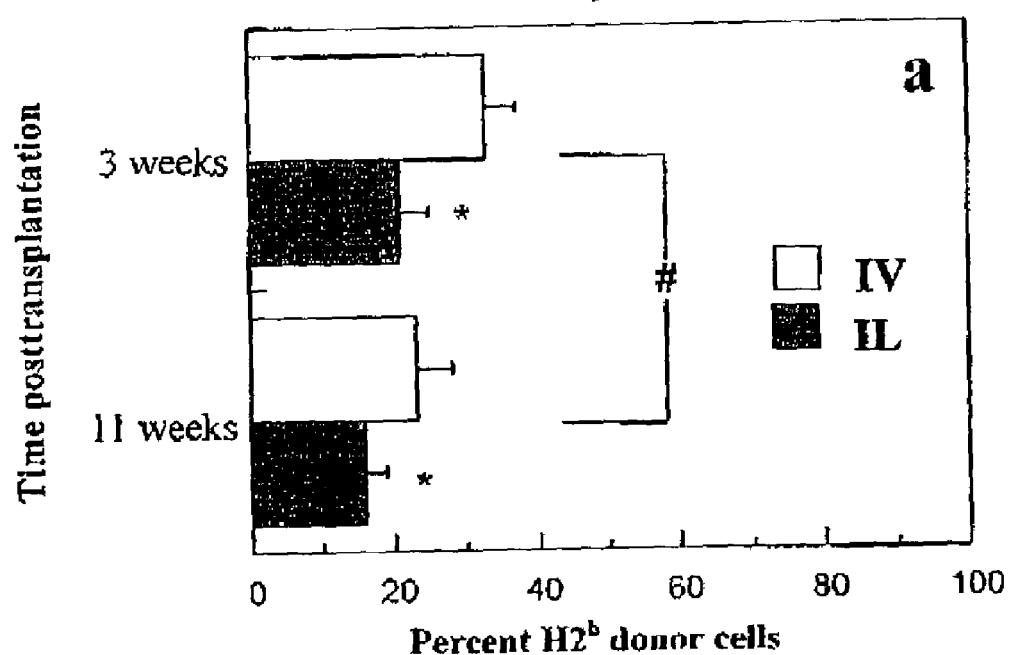
FIGS. 5a–b are histograms depicting the levels of donor specific hemopoietic chimerism 4 and 11 weeks following injection of $10^7$ cells from B10 donors ($H2^b$) via IV-BMT (IV) or IL-BMT (IL) into BALB/c ($H2^d$) recipients conditioned sublethally with 35 μg/g busulfan.
Figure 5B:
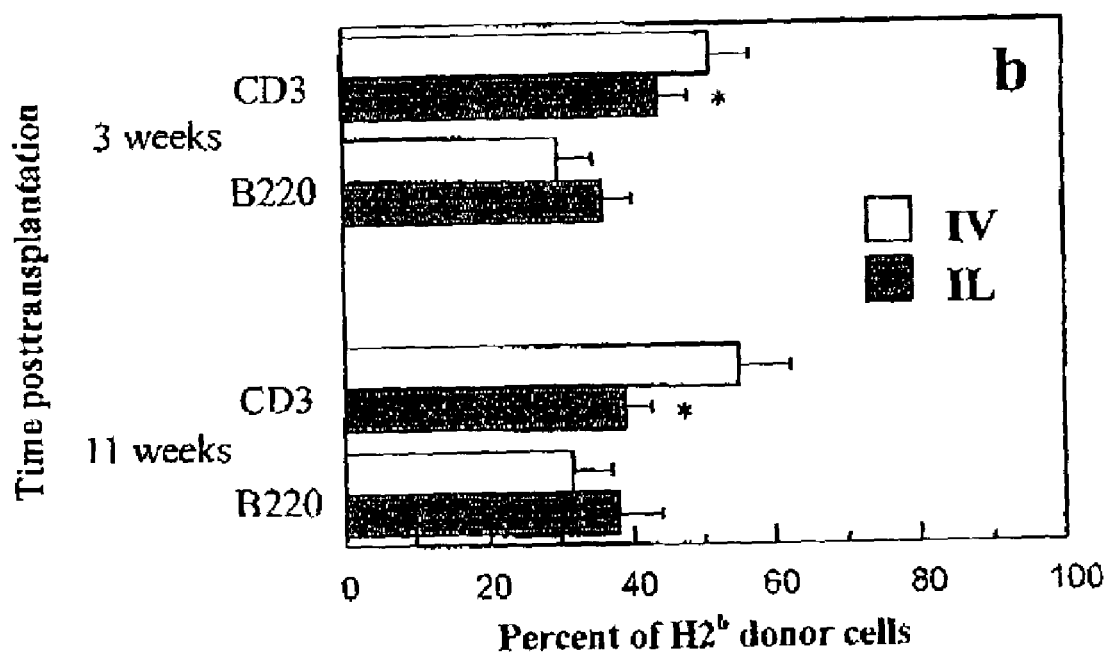

As shown in FIG. 5b, the method of the present invention can be used to induce multilineage hemopoietic chimerism. It will be appreciated that such induction of multilineage hemopoietic chimerism can be used to treat diseases such as the aforementioned diseases.

Without wishing to be bound by theory, it is believed that donor specific hemopoietic chimerism, with which induction of tolerance of secondary donor grafts by bone marrow cell transplantation is correlated, requires engraftment of donor bone marrow cells in the bone marrow, the only site that hosts efficient long-term multilineage hematopoiesis (Nibley W E. and Spangrude G J., 1998. Bone Marrow Transplant. 21:345).

In addition to applicability in the context of replacement transplantation described above, the method of the present invention can be used to induce tolerance to transplants transplanted in the context of adoptive therapy. Conditions for which this therapeutic modality is applicable include, but are not limited to, malignant, viral, autoimmune and parasitic diseases. Such adoptive cell therapies can be employed, for example, towards treatment of congenital or acquired immunodeficiency syndrome (AIDS) via transplantation of donor-derived immune effectors, such as T lymphocytes or natural killer (NK) cells directed, either naturally or due to genetic modification, against cells expressing tumor-associated or human immunodeficiency virus (HIV) antigens, respectively.

The method of the present invention can further be used to treat diseases, disorders, or conditions associated with autoimmunity including, but not limited to, insulin dependent diabetes (type I), multiple sclerosis, systemic lupus erythematosus, rheumatoid arthritis and scleroderma. As has been demonstrated in the literature of the art, bone marrow cell transplantation can be employed to treat autoimmune diseases (Burt R K. et al., 2002. Blood 99(3):768–84; Moore J. and Brooks P., 2001. Springer Semin Immunopathol. 23(1–2):193–213; Ikehara S., 2001. Exp Hematol. 29(6): 661–9).

Since bone marrow cell transplantation induces tolerance concomitantly with engraftment of transplanted bone marrow cells in bone marrow tissue of the subject, the method according to this aspect of the present invention is preferably effected by administering the dose of bone marrow cells to a body part containing a bone tissue, which bone tissue preferably being a bone marrow tissue.

Figure 2A:
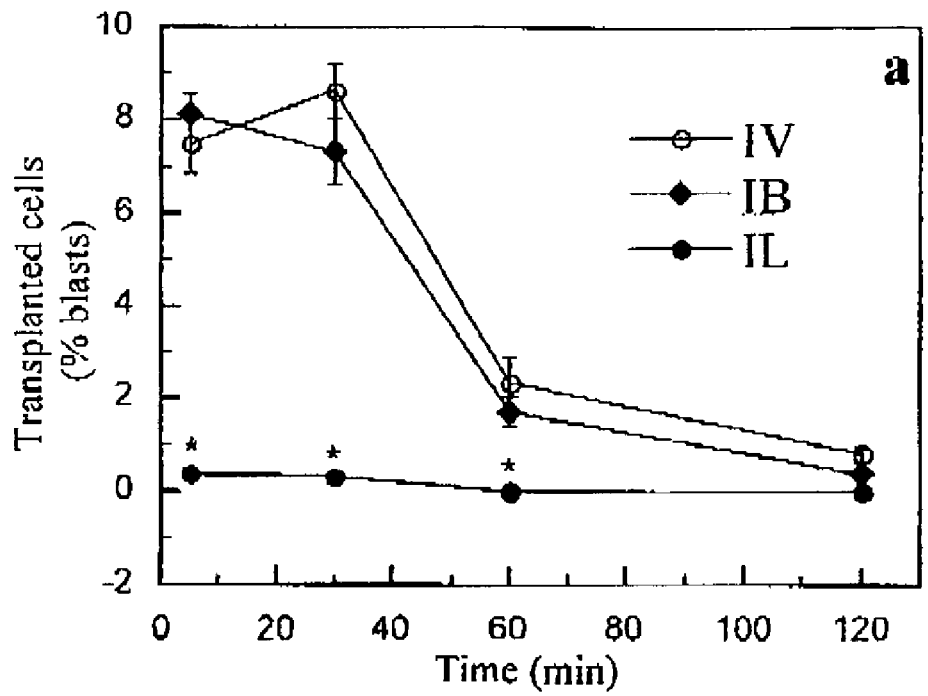
FIGS. 2a–b depict the distribution of transplanted BMCs at various time points following intravenous BMT (IV-BMT), IB-BMT, and IL-BMT. Supralethally conditioned B10.BR recipients were injected with $5 \times 10^7$ syngeneic whole BMCs labeled with fluorescent PKH67 membrane linkers (n=5), and percentages of PKH-positive BMCs were measured in peripheral blood at various time points following transplantation (FIG. 2a), and in injected and contralateral (non-injected) femurs two hours following transplantation (FIG. 2b). Percentages of PKH-positive cells were measured by flow cytometry via gating on blasts. Percentages of cells in contralateral femurs following IV-BMT represent the mean of the two femurs. Data represent mean ± standard deviation (*$p<0.05$).
Figure 2B:
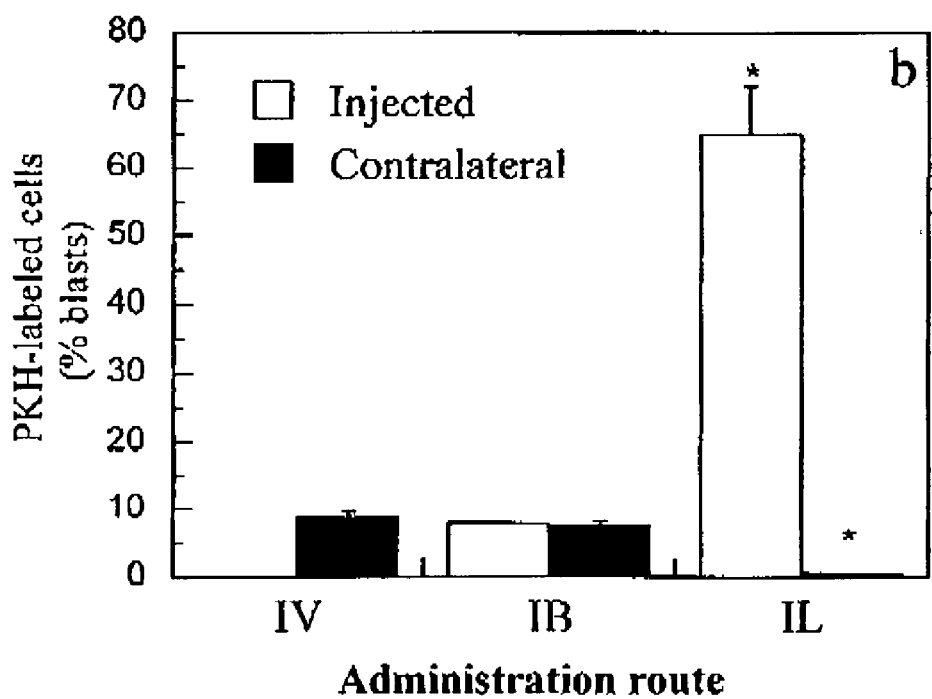

Fluid flow restriction in the body part containing the bone tissue prevents dissemination of administered bone marrow cells away from the body part, and thereby results in optimal homing or retention of administered bone marrow cells to the bone tissue contained in the body part relative to prior art methods, as shown in FIGS. 2a–b of the Examples section which follows. As described further hereinbelow, the increased homing of bone marrow cells to bone tissue achieved by the method according to this aspect of the present invention correlates with superior induction of tolerance relative to prior art methods.

In order to optimize homing or retention of administered bone marrow cells to the bone tissue, fluid flow restriction is preferably effected prior to administration of bone marrow cells, so as to optimize retention of administered bone marrow cells in the body part containing the bone tissue.

Without wishing to be bound by theory, it is believed that infusion of a large number of cells into such a small, flow-restricted hematopoietic space: creates a local "megadose effect" that may provide significant advantages for initial bone marrow cell engraftment (Saxe D. et al., 1984. Exp Hematol. 12:277; Wu D. and Keating A., 1993. Exp Hematol. 21:251; Stewart F. et al., 1993. Blood 81:2566; Bachar-Lustig B et al., 1995. Nat Med. 1: 1268; Rao S S. et al., 1997. Exp Hematol. 25:114;; Gandy K L, Weissman I L., 1998. Transplantation 65:295; Uchida N. et al., 1998. J Clin Invest. 101:961; Reisner Y. and Martelli M F., 2000. Exp Hematol. 28:119); may overcome antigenic barriers presumed to restrict their interaction with host bone marrow stromal microenvironment (Hashimoto F. et al., 1997. Blood 89:49; Sugiura K. et al., 2001. Stem Cells 19:46; Rao S S. et al., 1997. Exp Hematol. 25:114; Askenasy N and Farkas D L., 2002. Stem Cells 20:80); enables improved competitiveness of the large number of administered bone marrow cells for vacant niches of engraftment (Saxe D. et al., 1984. Exp Hematol. 12:277; Wu D. and Keating A., 1993. Exp Hematol. 21:251; Stewart F. et al., 1993. Blood 81:2566); and enables avoidance of depletion, modification or degradation of inoculum during systemic circulation. As is widely accepted in the art, the majority of bone marrow cells injected intravenously are entrapped in the liver, spleen, lungs, lymph nodes and thymus of the subject, decreasing the net number of cells that home to the bone marrow tissue (Martin P J., 1992. Blood 79:1647; Lahiri S K. and van Putten L M., 1969. Cell Tissue Kinet. 2:21; Testa N G. et al, 1972. Blood 40:654; Hendrikx P J. Et al., 1996. Exp Hematol. 24:129; Cui J. et al., 1999. Br J Haematol. 107: 895; Lanzkron S M. et al., 1999. Blood 93:1916; Szilvassy S J. et al., 1999. Blood 93:1557; Askenasy N and Farkas D L. In vivo imaging studies of the effect of recipient conditioning, donor cell phenotype and antigen disparity on homing of haematopoietic cells to the bone marrow. 2002. Br. J. Haematol. In press).

As previously stated hereinabove, the dose of cells is preferably administered via injection into a blood vessel of the portion of the circulatory system.

As shown in the following Examples section, such administration into the portion of the circulatory system results in optimally efficient homing or retention of administered bone marrow cells to the bone marrow, and consequently in optimal donor specific tolerance induction.

As previously stated hereinabove, tourniquet application may be advantageously employed to restrict fluid flow.

Since tourniquet application may be conveniently applied to a limb, and since limbs contain significant quantities of bone marrow tissue, the body part is preferably a limb or a portion thereof containing a bone marrow tissue. Since the upper portion of the femur is the portion of a limb having the greatest quantity of bone marrow tissue, the portion of the circulatory system is preferably delimited by a leg, more preferably by the upper thigh.

Application of a tourniquet at the top of the leg can be advantageously used to effectively promote bone marrow tissue homing of bone marrow cells administered intravenously to the leg, and to thereby efficiently induce tolerance to a transplant, as described in the Examples section below.

The dose of bone marrow cells may be obtained using various methods, depending on the application and purpose. For example, the dose of bone marrow cells may be obtained as human CD34-positive hematopoietic stem cells mobilized into the peripheral blood by cytokine treatment and harvested via leukapheresis, or more preferably, via harvest of whole bone marrow cells, for example, via aspiration from the iliac crest of the femur.

Methods of obtaining bone marrow cells, such as the methods described above, are standardized and widely employed in the art. Ample guidance for such practice is provided by the literature of the art (for example, refer to: Repka T. and Weisdorf D., 1998. Curr Opin Oncol. 10:112–7; Janssen W E. et al, 1994. Cancer Control 1:225–230; Atkinson K., 1999. Curr Top Pathol. 92:107–36).

Depending on the purpose and application, the dose of bone marrow cells may be administered as a fractionated dose, or more preferably as a single dose.

A suitable dose of bone marrow cells for inducing long-term donor specific hemopoietic chimerism, according to this aspect of the present invention, is less than or equal to a number of cells per kilogram body weight selected from the range of about 40 million cells per kilogram body weight to about 2 billion cells per kilogram body weight.

Figure 3A:
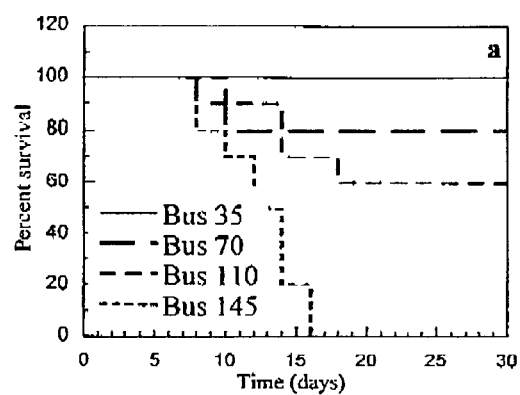
FIGS. 3a–d depict peripheral blood levels of transplanted BMCs in busulfan conditioned recipients following IV-BMT or IL-BMT.
Figure 3B:
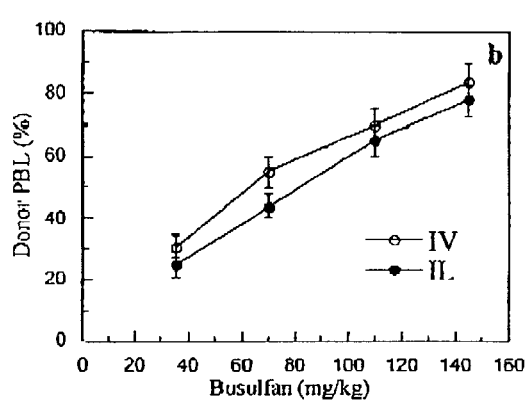
Figure 3C:
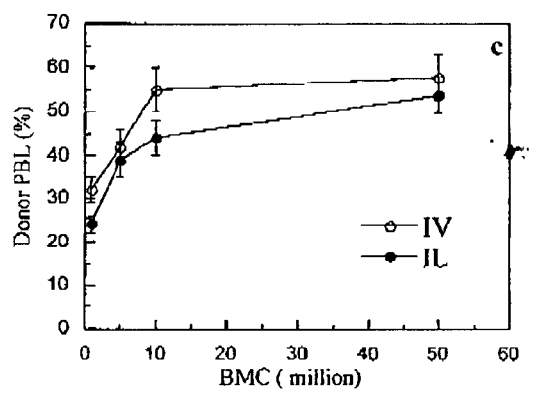

Desired levels of donor specific hemopoietic chimerism may be obtained by modulating the dose of administered bone marrow cells, with levels of chimerism increasing with the size of the bone marrow cell inoculum, as described in the Examples section below, and as is illustrated in FIG. 3c.

As used herein, doses of bone marrow cells described as numbers of cells per kilogram body weight are extrapolated from doses described in the Examples section below on the basis of an average 8 to 10 week-old mouse weighing about 25 grams.

According to the present invention, a suitable dose of bone marrow cells for inducing tolerance to an organ transplant, such as a cardiac transplant, or a tissue transplant, such as a skin transplant, is less than or equal to about 400 million cells per kilogram body weight.

As described in the following Examples section, administering a dose of 400 million bone marrow cells per kilogram body weight, according to this aspect of the present invention, can be used to induce long-term tolerance to an organ transplant, such as a cardiac transplant, or a tissue transplant, such as a skin transplant.

Depending on the purpose and application, the dose of bone marrow cells, according to the present invention, may be a dose of T-cell depleted bone marrow cells or a dose whole bone marrow cells.

Figure 3D:
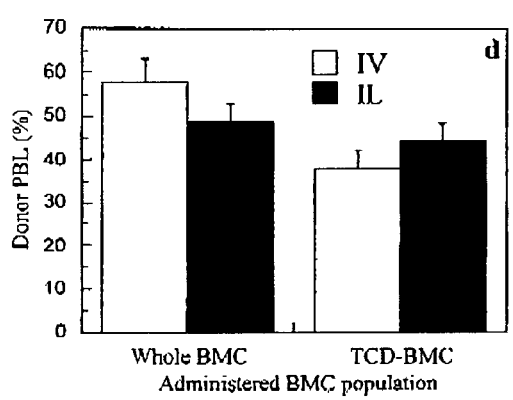

It will be appreciated by one of ordinary skill in the art that T cell depletion of a bone marrow cell transplant can be used to reduce the incidence of graft-versus-host disease. As described in the Examples section which follows and as illustrated in FIG. 3d, administration of a dose of T cell depleted bone marrow cells, according to this aspect of the present invention, can be used to rescue lethally conditioned subjects while inducing higher levels of donor specific hemopoietic chimerism in such subjects, as compared to prior art methods employing systemic (intravenous) administration of a dose of T cell depleted bone marrow cells.

As described in the following Examples section, a dose of whole bone marrow cells can be used according to the method of the present invention to induce long-term donor specific hemopoietic chimerism, and long-term tolerance to a donor-derived organ or tissue transplant.

According to the method of the present invention, the dose of bone marrow cells is preferably a dose of nucleated bone marrow cells.

Further according to the method of the present invention, the dose of bone marrow cells is preferably a dose of erythrocyte depleted bone marrow cells.

Still further according to the method of the present invention, the subject may be advantageously conditioned prior to administering the dose of cells in order to facilitate engraftment thereof, in particular prior to administering an allogeneic cell dose such as an allogeneic bone marrow cell dose.

As used herein, the term "conditioning" refers to a treatment resulting in at least a partial loss of an immunological defense or in at least a partial loss of a hemopoietic capacity, which loss or losses acting to facilitate engraftment or tolerance of the transplant.

Depending, for example, on the type of transplant and the condition of the subject, the subject may be conditioned under sublethal, lethal or supralethal conditions.

As used herein, "sublethal conditioning" refers to conditioning being typically non-lethal to all members of a population of subjects to which such conditioning is applied, "lethal conditioning" refers to conditioning which is typically lethal to some but not all members of a population of subjects to which such conditioning is applied, and supralethal conditioning refers to conditioning which is typically lethal to all members of a population of subjects to which such conditioning is applied.

One example of supralethal conditioning is myeloablative conditioning, in which sufficient hemopoietic or immunological capacity to ensure survival is eliminated in essentially all subjects to which such conditioning is applied. One example of lethal conditioning is myeloreductive conditioning, in which sufficient hemopoietic capacity to ensure survival is retained in a substantial fraction of subjects to which such conditioning is applied.

Depending on the application and purpose, conditioning may be effected, for example, by any combination of irradiation, treatment with a myeloablative agent, and/or treatment with an immunosuppressive agent, according to standard protocols.

Conditioning may be effected using biological methods, for example by administration of anti graft immunity-suppressing cells or by administration of biological molecules capable of inhibiting anti graft immunoreactivity, such as, for example, Fas-ligand and CTLA4-Ig.

Examples of myeloablative agents include busulfan, dimethyl mileran, melphalan and thiotepa.

Examples of immunosuppressive agents include prednisone, methyl prednisolone, azathioprine, cyclosporine A, cyclophosphamide, fludarabin, CTLA4-Ig, anti-T cell antibodies, etc.

A sublethal dose of irradiation is within the range of 1 to 7.5 Gy whole body irradiation, a lethal dose is within the range of 7.5 to 9.5 Gy whole body irradiation and a supralethal dose is within the range of 9.5 to 16.5 Gy whole body irradiation.

Depending on the purpose and application, the dose of irradiation may be administered as a single dose or as a fractionated dose.

According to a preferred embodiment, conditioning comprises administering a dose of irradiation essentially exclusively to the body part or to a portion thereof, so as to induce myeloreduction or myeloablation essentially exclusively in the body part or the portion thereof. As is widely recognized in the art, a subject can tolerate as sublethal conditioning ultra-high levels of selective irradiation to a body part such as a limb, which levels constituting lethal or supralethal conditioning when used for whole body irradiation.

Such selective irradiation of the body part, or portion thereof, can be advantageously utilized to achieve engraftment of administered bone marrow cells, which engraftment correlating with greater tolerogenicity than that resulting from administration of bone marrow cells via all prior art methods, as described hereinbelow.

The dose of irradiation suitable for inducing myeloreduction or myeloablation essentially exclusively in the body part or portion thereof can easily be extrapolated from the data provided in the following Examples section, as well as from the literature of the art (for example, refer to Breitz H., 2002. Cancer Biother Radiopharm. 17:119; Limit S M., 1997. J Nucl Med. 38:1374; Dritschilo A. and Sherman D S., 1981. Environ Health Perspect. 39:59). An ordinarily skilled artisan such as, for example, a physician or medical radiologist, possesses the expertise required for correct administration of such a dose of irradiation.

As described in the Examples section which follows, administration of a dose of bone marrow cells in conjunction with conditioning consisting only of a selective dose of irradiation to the body part. according to the method of the present invention can be used to induce long-term tolerance to a donor-derived tissue graft, such as a skin graft, without the need for posttransplant immunosuppression. Furthermore, as also described in the Examples section which follows, such tolerance induction is achieved with extremely low levels of donor specific hemopoietic chimerism, which levels being as low as 1%.

It will be appreciated by the skilled practitioner that such results are highly unexpected since it is a prior art paradigm that levels of hemopoietic chimerism will correlate with levels of donor specific tolerance induction, and that conditioning intensity must be increased to compensate for low levels of hemopoietic chimerism in order to achieve similar secondary graft tolerance.

By enabling minimization of conditioning, the method of the present invention provides the critical advantage of enabling the hematopoietic system of the subject to recover in time to prevent death due to opportunistic infection. The general unavoidability of such a period of exposure to lethal infections is a major drawback of prior art lethal or supralethal conditioning regimens (Sharabi Y. and Sachs D., 1989. J Exp Med. 169:493; Markus P M. et al., 1993. Cell Transplant. 2:345; Armitage J O., 1994. New Engl J Med. 330:827; Tomita Y. et al., 1994. Blood 83:939; Colson Y L. et al., 1995. J Immunol.155:4179; Colson Y. et al., 1995. Transplantation 60:971; Colson Y. et al., 1996. J Immunol. 157:2820; Tomita Y. et al., 1996. Transplantation 61:469; Pearson T C. et al., 1996. Transplantation 61:997; Sykes M. et al., 1997. Nat Med. 3:783; Gammie J S. et al., 1998. Circulation 98(Suppl. II):163; Kushida T. et al., 2000. Blood 95:1862; Kushida T. et al., 2001. Blood 97:3292).

Thus, the method of the present invention is significantly superior to all prior art methods of inducing tolerance to tissue allografts, since such methods require, for example, lethal or supralethal conditioning regimens, and significantly higher levels of hemopoietic chimerism than those required according to this aspect of the present invention.

According to the method of the present invention, conditioning may advantageously comprise administration of a dose of a myeloablative agent, which myeloablative agent preferably being busulfan.

Depending on the application and purpose, the administered dose of the myeloablative agent may be sublethal, lethal, or supralethal (myeloablative). Suitable guidance regarding administration of sublethal, lethal or supralethal doses of a myeloablative agent such as busulfan is available in the literature of the art (for example, refer to: Hassan M. et al., 1996. Leuk Lymphoma 22:395; Buggia I. et al., 1994. Ann Pharmacother. 28:1055).

According to the teachings of the present invention, the dose of busulfan is preferably less than or equal to a number of milligrams per kilogram body weight selected from a range of about 35 milligrams per kilogram body weight to about 145 milligrams per kilogram body weight.

Extrapolation of the success of engraftment of transplanted bone marrow cells with irradiation-based protocols suggests that doses of busulfan of about 35–70 milligrams per kilogram body weight are equivalent to whole body irradiation doses of about 400–700 rad (Mauch P. et al., 1988. Transplantation 46:205; Yeager A M. et al., 1991. Blood 78:3312; Down J D. and Ploemacher R E., 1993. Exp Hematol. 21:913; Colson Y L. et al., 1995. J Immunol 155:4179).

Depending on the purpose and application, the dose of myoablative agent may be administered as a single dose or as a fractionated dose.

As described in the Examples section which follows, administration of a sublethal dose of busulfan according to the method of the present invention can be used to induce long-term tolerance to a donor-derived organ transplant, such as a cardiac transplant, and to induce long-term tolerance to the administered bone marrow cells, as evidenced by the resultant donor specific hemopoietic chimerism.

As further described in the Examples section which follows, administration of a non-myeloablative dose of busulfan according to the teachings of the present invention can be used to induce long-term tolerance to donor-derived tissue transplants, such as a skin transplants.

As yet further described in the Examples section which follows, the method according to this aspect of the present invention can be used to rescue subjects administered a myeloablative dose of busulfan with less graft-versus-host disease relative to prior art methods employing intravenous administration of bone marrow cells to induce hemopoietic chimerism.

Without wishing to be bound by theory, it is believed that concentrating the dose of bone marrow cells in the body part according to the method of the present invention may optimize the local stem cell engraftment-supporting effect of T-cells (El-Badri N S. and Good R A., 1993. PNAS 90:6681; Gandy K L et al, 1999. Immunity 11:579; Askenasy N et al., 2002. Stem Cells 20:301) while minimizing effects resulting from systemic dissemination leading to graft-versus-host disease (Vallera D A. and Blazar B R., 1989.

Transplantation 47:751; Bachar-Lustig B et al., 1995. Nat Med. 1:1268; Andrews R G. et al., 1992. Blood. 80:1693; Lapidot T. et al., 1992. Blood. 80:2406; Drobyski W R and Majewski D. 1997. Blood. 89:1100; Gandy K L et al., 1999. Immunity 11:579).

According to the method of the present invention, the dose of bone marrow cells may be administered prior to, concomitantly with or following transplantation of the transplant, depending on the context and purpose of the application.

According to the teachings of the present invention, the dose of bone marrow cells is advantageously administered prior to transplantation of the transplant, so as to enable optimal engraftment of the administered bone marrow cells, the concomitant development of optimal hemopoietic chimerism, and the resultant optimal induction of donor specific tolerance.

Alternately, essentially simultaneous administration of the dose of bone marrow cells and transplantation of the transplant may be highly advantageous in certain circumstances, such as, for example, when organs and cells for transplantation are harvested from cadaveric donors and their ex-vivo preservation is limited in time (Askenasy N. et al, 1995. Am J Physiol. 269:H1056; Askenasy N. et al., 1996. J Mol Cell Cardiol. 28:589; Askenasy N. and Navon G., 1998. J Mol Cell Cardiol. 30:1329; Askenasy N. et al., 1999. J Mol Cell Cardiol. 31:1795).

As described in the Examples section below, administration of the dose of bone marrow cells simultaneously with transplantation of a transplant, such as a skin transplant, can effectively induce long-term tolerance to the transplant. As such, the method of the present invention is superior to all prior art methods, being unique in having demonstrated such capacity.

Without wishing to be bound by theory, it is believed that such effective tolerization following such simultaneous administration of the dose of bone marrow cells to a flow-restricted portion of the circulatory system and the transplant according to the method of the present invention may at least be partially due to a critically rapid bone marrow engraftment of the administered bone marrow cells and release of donor progeny thereof.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al, "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Transplantation of Allogeneic Donor Bone Marrow Cells Via Isolated Limb Perfusion Effectively Induces Immunological Tolerance to Donor Type Skin and Cardiac Grafts in Mildly Conditioned Recipients Transplantation of allogeneic cells, tissues and organs is a major life-saving and therapeutic modality for numerous diseases. However, such transplantation is beset by numerous problems, including graft rejection and graft-versus-host disease which must be inhibited by the use of highly toxic immunosuppressive agents. Transplantation of megadoses of allogeneic donor BMCs in conjunction with pre-conditioning with total body irradiation has been shown to lead to stable engraftment of donor BMCs, and to consequent donor specific hemopoietic chimerism, which chimerism having been shown to correlate with induction of immunological tolerance to secondary donor type organ grafts without or with mild posttransplantation immunosuppressive regimens (Ildstad S T and Sachs D H. 1984. Nature 307:168; Sharabi Y and Sachs D. 1989. J Exp Med 169:493; Bachar-Lustig B et al., 1995. Nat Med 1:1268; Uchida N. et al., 1998. J Clin Invest. 101:961; Reisner Y. and Martelli M F., 2000. Exp Hematol. 28:119). However, this approach is suboptimal since whole body irradiation entails undesirable side-effects, and the megadoses of BMCs required, whose effects have been demonstrated in mice, are not practicably harvestable in humans. While reducing the present invention to practice as follows, the present inventors have uncovered that transplanting allogeneic donor BMCs into a restricted hematopoietic space without pre-conditioning with whole body irradiation can be used to locally achieve the same effect as that obtained by systemic infusion of a megadose of BMCs.

Materials and Methods:

Animals and recipient preparation: B10 (C57Bl/10Sn, $H2^b$), B10.BR (C57Bl/SgSn, $H2^k$) and Balb/c ($H2^d$) mice purchased from Jackson Laboratories (Bar Harbor, Me.) were housed in a pathogen-free facility. Mice aged 8–10 weeks were anesthetized by intraperitoneal injection of 12–17 micrograms Avertin/g body weight (Sigma Chem. Co., St Louis, Mo.). Recipients were conditioned by intraperitoneal injection of busulfan 36 hours prior to transplantation. Busulfan was dissolved in dimethyl sulfoxide (DMSO) at a concentration of 24 mg/ml and the solution was diluted five-fold in water at 40° C. prior to injection. For localized conditioning, the limb prepared for IL-BMT was irradiated with a total dose of 950 rad, at a rate of 105 rad/min from a cesium source (J.L. Shephard & Assoc., San Fernando, Calif.).

Isolation of BMCs: Bone marrow cells were harvested from femurs and tibias crushed in Hank's balanced salt solution (HBSS, Gibco Laboratories, Grand Island, N.Y.). Bone marrow cells were suspended using an 18G needle, the suspension was filtered with a 30 micron sterile nylon mesh, the cells were collected by centrifugation (400×g, 10 minutes, 4° C.) and resuspended in HBSS supplemented with 2% fetal calf serum (FCS). Erythrocytes were lysed by incubation with ammonium chloride for 4 minutes at room temperature. Nucleated cells (whole BMCs) were counted following two washes with excess medium.

T cell depletion was performed by incubating BMC suspensions with rat-anti mouse CD4 monoclonal antibody and rat-anti mouse CD8 monoclonal antibody (both obtained from Pharmingen, San Diego, Calif.) for 30 minutes at 4° C. Excess rat antibody was removed by two washes with PBS supplemented with 2% FCS. Then cells were then gently mixed with goat-anti rat IgG conjugated to M-450 magnetic beads at a ratio of 4 beads per cell (Dynal Inc., Lake Success, N.Y.) for 20 minutes at 4° C. T cells rosetted with beads were magnetically separated and the T cell-depleted supernatant was collected. Depletion of T cells was assessed by flow cytometry (Coulter Elite, Miami, Fla.) using FITC-labeled anti αβ-TCR monoclonal antibodies.

PKH-labeling of donor cells: To enable monitoring of administered donor cells, aliquots of $2 \times 10^7$ cells were suspended in 1 ml of Diluent C of PKH membrane linker kit and freshly prepared PKH67 membrane linker was added to a final concentration of 2 micromolar according to the manufacturer's instructions (Sigma Chem. Co., St. Louis, Mo.). Samples were then incubated at room temperature for 5 minutes with gentle mixing. Staining was terminated by addition of 4 volumes HBSS supplemented with 10% FCS, and the cells were collected by centrifugation (400×g, 10 minutes, 4° C.) and washed twice with HBSS. The average BMC recovery of the procedure was 90%, with a viability of 95%, as determined by trypan blue exclusion. It has been shown that PKH-labeling does not qualitatively or quantitatively alter cellular homing and seeding in recipient bone marrow (Askenasy N and Farkas D L. Optical imaging of PKH-labeled hematopoietic cells in recipient bone marrow in vivo. Stem Cells. in press).

Administration of BMCs: For intravenous bone marrow transplantation (IV-BMT), BMCs suspended in phosphate buffered saline (PBS) were injected into the lateral tail vein of heat-treated recipients.

For isolated-limb bone marrow transplantation (IL-BMT), blood flow to the limb was occluded with a proximal tourniquet, and the femoral artery and vein were clamped and cannulated with needle-guided 24 G catheters (FIG. 1a). Surgery was performed using a Leica GZ6 surgical stereoscope (Northvale, N.J.). Cells were suspended in 2 ml Krebs-Henseleit physiological solution (KH). The KH perfusion medium was aerated with a mixture of 5% $CO_2$/95% $O_2$ to give a final pH of 7.3, and was warmed to 37° C. in a double-walled water-jacketed container, as previously described (Askenasy N. and Navon G., 1997. J Mol Cell Cardiol. 29:1715). The femoral artery was perfused in three stages at a rate of 0.2 ml/min using a miniperistaltic pump, as follows: first 5 minutes with KH, then with donor cells in KH ($0.5 \times 10^6$ cells/ml to $10^8$ cells/ml) and finally 10 minutes with KH. Such low infusion volume was employed to minimize extravasation and accumulation of cells in the soft tissues of the limb. Outflow from the femoral vein was collected into a container and the femoral vein was occluded following perfusion, diverting blood drainage from the limb to the deep veins. Flow through the femoral artery was restored either by a side-to-side anastomosis, ligation to a short segment of the 24G catheter, or repair of the site of cannule insertion. The limb was gradually reperfused by intermittent release of the arterial clamp.

Figure 1B:
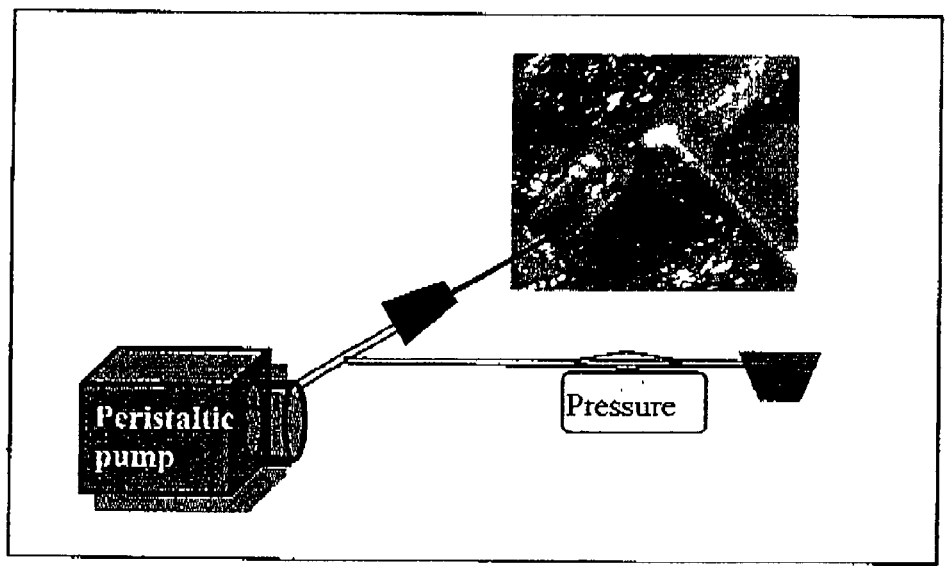

For intra-bone marrow bone marrow transplantation (IB-BMT), the knee was exposed by a sharp skin incision, the knee was flexed, and a 24G needle was inserted into distal femoral epiphysis above the patella (FIG. 1b). Donor BMCs suspended in phosphate-buffered saline (PBS) were injected into the femur using a miniperistaltic pump (P720, Instech, Plymouth Meeting, Pa.) via a double outlet system. Cells were infused through one outlet at a rate of approximately 20 to 50 microliters per minute, and the other outlet, used for outflow, was connected to a threshold pressure transducer and a PowerLab monitoring system (ADInstruments, Grand Junction, Colo.). When intraluminal pressure increased above a threshold value (8 or 20 mm Hg), the medium was diverted into a drainage reservoir.

Kinetics of systemic scattering of BMCs: Blood samples were collected into heparinized serum vials in 200 microliters HBSS, washed twice and collected by centrifugation (400×g, 10 minutes, 4° C.). Femurs of recipients of PKH-labeled cells were harvested from mice euthanized by $CO_2$ asphyxiation under anesthesia, and BMCs were collected from bones crushed in HBSS. Following lysis of erythrocytes the fraction of PKH-positive cells was determined by flow cytometry on the blast gate. When the number of PKH-positive cells was low samples were screened with a fluorescence microscope (Axiophot, C. Zeiss).

Characterization of donor chimerism: Blood samples were collected into heparinized serum vials in a volume of 200 microliters in HBSS and were incubated with fluorochrome-labeled monoclonal antibody as follows: PE-labeled anti $H2^b$ monoclonal antibody for detection of B10 donor-derived cells, FITC-labelled anti $H2^k$ for detection of B10.BR recipient-derived cells, and FITC-labelled anti $H2^d$ monoclonal antibody for detection of Balb/c recipient-derived cells. Blood cells were layered over 1.5 ml lymphocyte separation media (1.087 g/ml, CedarLane, Ontario, Canada). Following centrifugation (1000×g, 20 minutes, 4° C.) low density cells were collected, washed twice with HBSS and fixed with 0.5% paraformaldehyde. The percentage of PE-positive donor ($H2^b$) peripheral blood lymphocytes (PBL) was determined by flow cytometry on the lymphocyte gate.

For determination of the percentages of donor specific T cells and B cells, cells were labeled with FITC-conjugated anti-CD3 or FITC-anti-B220 monoclonal antibody, respectively.

For determination of the percentages of $SCA-1^+$ $c-kit^+$ lineage$^-$ stem cells in host femurs, cells were isolated from bones as described above. The cells were incubated with biotinylated anti-$H2^b$ monoclonal antibody, washed twice with PBS supplemented with 1% bovine serum albumin (BSA), and incubated with excess streptavidin conjugated to M-450 magnetic beads (Biotin Binder Kit, Dynal Inc., Lake Success, N.Y.). Rosetted donor cells were precipitated by exposure to a magnetic field and the supernatant containing non-$H2^b$ cells was removed. Donor BMCs were resuspended and treated with deoxyribonuclease according to the manufacturer's instructions. These cells were incubated with PE-conjugated anti SCA-1 antibodies, allophycocyanin conjugated-anti c-kit antibody and a cocktail of FITC-labeled mAbs specific for the lineage markers CD5, GR-1, CD45R, Ly-76, TCR-αβ and TCR-γδ (Pharmingen, San Diego, Calif.). Analysis of donor cells was performed by flow cytometry.

Skin grafting: Full-thickness tail skin from BMC-matched and third party donors was grafted in the inter-scapular region of anesthetized chimeras (Barker C F. and Billingham R E., 1996. Surg Forum 17:480). Grafts were inspected on a daily basis for signs of rejection, and disappearance of the epidermis was considered as complete rejection.

Heterotopic heart transplantation: Hearts were transplanted as vascularized grafts into naive recipients and chimeras, as previously described (Ono K. and Lindsey E S., 1969. J Thorac Cardiovasc Surg. 57:225–259). Briefly, hearts were harvested from donors euthanized by $CO_2$ asphyxiation and cooled on ice throughout the surgical procedure. The intra-abdominal aorta and inferior vena cava of recipients were exposed, and connected to the graft aorta and pulmonary artery, respectively, via end-to-side anastomoses. Grafts resumed spontaneous contraction upon warming and reperfusion. Cardiac function was monitored daily by palpation and rejection was determined when contraction ceased.

Assessment of graft-versus-host disease: Recipients were evaluated for signs of graft-versus-host disease on a daily basis for the first month following BMT and at three days intervals thereafter. Diagnosis of graft-versus-host disease was based on the previously described manifestations of diffuse erythema (particularly of the ear), hyperkeratosis of the foot pads, dermatitis, unkempt appearance, weight loss, or diarrhea (Hoffman A L, et al., 1989. Surgery 106:354–363). Graft-versus-host disease was diagnosed by histological analysis of the tongue or skin at the time of autopsy. Ear wedge biopsies were performed to evaluate the incidence of subclinical graft-versus-host disease. To evaluate the incidence of subclinical graft-versus-host disease, tissue was frozen and processed with routine hematoxylin and eosin staining for assessment of lymphoid infiltration, the presence of subepidermal clefts, or disappearance of the epidermis (Horn T D. et al., 1994. J Invest Dermatol. 103:206–210).

Statistical analysis: Data were calculated and presented as mean ± standard deviation for each experimental group. Within experimental groups reproducibility was evaluated by linear regression of duplicate measurements. Differences between the experimental groups were estimated via post-hoc Scheffe t-test at 5% level of significance.

Experimental Results:

In preliminary experiments the procedure of double cannulation of femoral artery and vein was established. The difficult stage of the surgical procedure was restoration of arterial blood supply. To avoid ischemic injury to the bone marrow limbs were perfused with oxygenated KH physiological solution, the average minimal duration being one hour. Low perfusion rates used in this study aimed to prevent accumulation of cells in soft tissues. The perfusion rates could be increased several fold without apparent injury to vascular endothelium, as assessed by perfusion with KH solution containing methyl blue. Limbs were flushed with medium to wash cells from the vasculature. Isolated limb perfusion caused an increase in creatine kinase activity in the peripheral blood of recipients from 29±4 (n=5) to 115±13 μmol/min/ml (n=15), indicating low levels of myocyte injury. Release of muscle enzymes was caused by the surgical procedure itself, and was observed in sham-operated mice, with and without arterio-venous perfusion. Initial studies were performed in a donor-recipient pair of B10 ($H2^b$) and B10.BR ($H2^k$), respectively. Subsequently, Balb/c ($H2^d$) recipients, which are white, were utilized, to facilitate monitoring of skin allografts from B10 mice, which are black.

Increased bone marrow homing/reduced peripheral dissipation following IL-BMT versus IB- or IV-BMT: The early distribution of transplanted donor BMCs labeled with PKH membrane linkers in peripheral blood and femurs of the recipients was assessed.

Peripheral blood was harvested at various time points following BMT and analyzed for donor cells. FIG. 2a demonstrates that very low levels of syngeneic donor BMCs were detected in the peripheral blood of lethally conditioned B10.BR recipients following IL-BMT whereas, in sharp contrast, high levels of donor BMCs were observed following IV-BMT and IB-BMT (p<0.05). Lowering the injection pressure to 8 mm Hg (n=3) did not change the profile of PKH-positive cells in peripheral blood.

Femurs were harvested 2 hours following BMT and their percentages of PKH-positive cells were quantified. FIG. 2b clearly demonstrates that IL-BMT resulted in very high levels of homing to the bone marrow, in sharp contrast to IB-BMT or IV-BMT. Following IL-BMT, femurs of the perfused limb were found to contain 58–65% PKH-positive BMCs (p<0.001 versus IV-BMT and IB-BMT) whereas flow cytometry did not detect PKH-positive cells in the contralateral femur. Detailed examination of the cellularity of the contralateral femurs by fluorescence microscopy revealed 12±3 (range 6–17) PKH-labeled cells 2 hours after IL-BMT, which increased 2.5 and 6 fold at 6 and 48 hours posttransplantation, respectively. In the case of IB-BMT no significant differences between the percentages of PKH-positive cells in the injected femur and the contralateral naive femur were observed. These femoral homing profiles did not change when the IB injection pressure was lowered to 8 mm Hg.

Differences in the cellular contents of femurs from the infused and contralateral limbs persisted for several weeks. At four weeks the femurs of the injected limbs contained $1.2 \times 10^7$ cells, which were 78±4% $H2^b$ donor specific (n=5). The contralateral femurs contained $0.32 \times 10^7$ cells in which only 47±5% were $H2^b$ donor specific (n=5, p<0.001 versus injected limb).

Figure 4A:
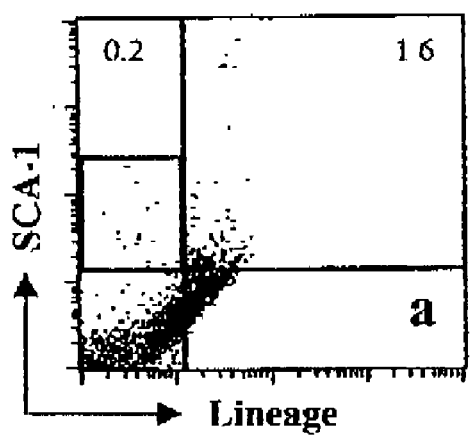
FIGS. 4a–d are flow cytometry dot plots depicting the differences in distribution of lin–SCA-1+c-kit+ hematopoietic stem cells in femurs of the infused (FIGS. 4a–b) and contralateral (FIGS. 4c–d) limbs 4 weeks following IL-BMT. Donor cells were immunomagnetically isolated and analysis was performed using FITC-labeled monoclonal antibodies against lineage markers, PE-anti SCA-1 and allophycocyanin-conjugated -anti c-kit mAb. Percent values are given in reference to the total number of donor cells ($H2^b$) in the host femoral bone marrow.
Figure 4B:
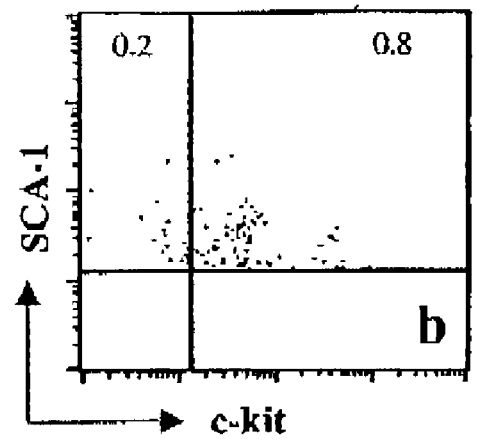
Figure 4C:
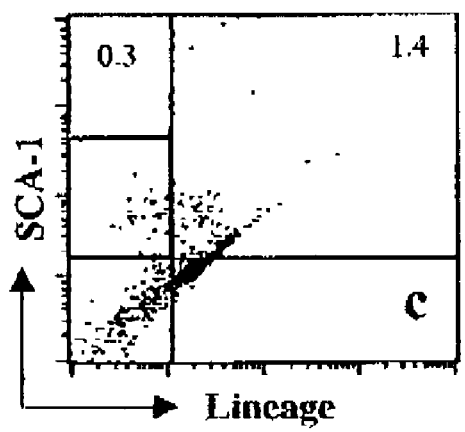
Figure 4D:
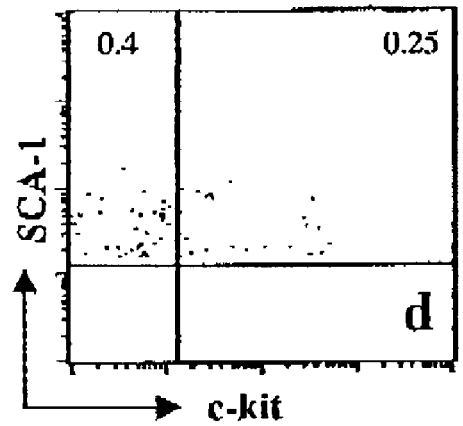

To assess whether hypocellularity of the non-infused femurs of the busulfan-ablated recipients offered favorable conditions for proliferation of a smaller number of progenitors that migrated to those bones, donor BMCs from both femurs (n=4 mice) were stained for SCA-1 and c-kit (Spangrude G J et al., 1988. Science 241:58; Okada S et al., 1991. Blood 78:1706). In the injected femurs 0.22±0.04% of the cells were SCA-1$^+$ lineage$^-$ (FIG. 4a) and 78±9% of these were c-kit$^+$ (FIG. 4b). In the contralateral femurs 0.31±0.04% of the cells were SCA-1$^+$ lineage$^-$ (FIG. 4c, p<0.001 versus injected limb) and 44±5% of these were c-kit$^+$ (FIG. 4d, p<0.001 vs injected limb).

Thus, the fraction of SCA-1$^+$ c-kit$^+$ lineage$^-$ cells in the contralateral femurs (0.07±0.01% of total cells) was significantly lower (p<0.01) than the fraction in the infused femurs (0.17±0.03% of total cells.)

These results clearly demonstrate that IL-BMT results in very high levels of homing to the bone marrow and results in very low levels of systemic dissipation of administered BMCs relative to IB-BMT or IV-BMT.

Optimization of IL-BMT and IB-BMT:

In order to optimize IL-BMT, the effects of conditioning, the size of the donor inoculum, T cell depletion, and the timing of donor BMC administration on hemopoietic chimerism and donor graft tolerance were analyzed.

Reconstitution of multilineage hematopoiesis in myeloreduced or myeloablated recipients via IL-BMT or IB-BMT: The 30-day survival of Balb/c recipients treated with doses of 35–145 micrograms busulfan/g body weight 36 hours prior to IV infusion of medium (without cells) is presented in FIG. 3a. A dose of 35 micrograms/g body weight was shown to constitute sublethal conditioning, doses of 70 and 110 micrograms/g body weight were shown to constitute lethal (myeloreductive) conditioning, and a dose of 145 micrograms/g body weight was shown to constitute supralethal (myeloablative) conditioning.

Administration of $10^7$ whole BMCs from B10 donors via IL-BMT or IV-BMT rescued Balb/c myeloreduced or myeloablated recipients conditioned with busulfan (n=5), and increasing doses of busulfan increased the levels of donor PBL chimerism at four weeks post-transplantation (FIG. 3b).

In similar experiments, administration of $5 \times 10^7$ syngeneic whole BMCs (B10.BR→B10.BR) via IV-BMT, IB-BMT or IL-BMT rescued all supralethally conditioned B10.BR recipients. Survival of supralethally conditioned B10.BR recipients was 100% following IV administration of allogeneic BMCs (B10→B10.BR) and was 90% (n=10) following IL and IB administration. After four weeks, the chimeras displayed 96±4, 91.5±5, and 78±4% donor lymphocytes in the IV-BMT, IB-BMT, and IL-BMT protocols, respectively. Graft-versus-host disease was diagnosed in 20% (2/10) of supralethally conditioned recipients treated with IV-BMT, and in none (0/10) of the supralethally conditioned recipients treated with IB-BMT or IL-BMT.

The 30-day survival rates following IV-BMT and IL-BMT administration of $10^7$ allogeneic (B10→BALB/c) whole BMCs were 90 and 80%, respectively (n=10 in each group). At four weeks the levels of $H2^b$ donor chimerism in the peripheral blood were 84±5 and 78±4% in the IV-BMT and IL-BMT protocols, respectively. In the IV-BMT treated hosts 44±5% and 35±5% of the $H2^b$ donor cells were CD3$^+$ and B220$^+$, respectively. In IL-BMT treated hosts 37±5% and 38±5% of the $H2^b$ cells were CD3$^+$ and B220$^+$, respectively.

These results clearly demonstrate that treatment with allogeneic IL-BMT or allogeneic IB-BMT can be used to reconstitute multilineage hematopoiesis in supralethally conditioned recipients, with less graft-versus-host disease than IV-BMT in the case of the latter.

Size of donor inoculum: Administration of increasing numbers of allogeneic BMCs (B10→Balb/c) into non-myeloablated recipients conditioned with 70 micrograms busulfan/g body weight increased the levels of donor chimerism (FIG. 3c) with similar near-maximal levels (approximately 55%) of donor chimerism being attained with administration of $1 \times 10^7$ cells and $5 \times 10^7$ cells via IV-BMT and IL-BMT, respectively (n=5).

Thus, IL-BMT is as efficient as IV-BMT for generation of donor specific PBL chimerism in non-myeloablated recipients.

Rescue of lethally conditioned recipients via IL-BMT with T cell depleted BMCs: The less efficient engraftment of T cell-depleted BMCs has been shown to be improved by infusion of megadoses of cells (Bachar-Lustig B. et al., 1995. Nat Med. 1:1268; Uchida N. et al., 1998. J Clin Invest. 101:961; Reisner Y. and Martelli M F., 2000. Exp Hematol. 28:119). To assess potential advantages of the megadose effect, Balb/c recipients lethally conditioned with 70 micrograms busulfan/g body weight were administered $10^7$ whole or T cell-depleted BMCs (n=10). While the fraction of donor PBLs decreased by 35% when T cell-depleted BMCs were administered via IV-BMT (p<0.001 versus whole BMCs), there was a non-significant decrease of 10% engraftment when T cell-depleted BMCs were administered via IL-BMT (FIG. 3d). The 30-day survival rates were 80% and 90% following transplantation of T cell-depleted BMCs via IV-BMT and IL-BMT, respectively.

Thus, IL-BMT of T cell depleted BMCs can be used to rescue lethally conditioned recipients.

Allogeneic IL-BMT induces multilineage allogeneic donor specific hemopoietic chimerism and long-term tolerance of cardiac allografts in sublethally conditioned recipients: Balb/c mice sublethally conditioned with 35 micrograms busulfan/g body weight and administered $10^7$ allogeneic BMCs from B10 donors via IV-BMT or IL-BMT (n=5–6) exhibited 33±4% and 21±4% (n=6, p<0.005) donor PBLs three weeks posttransplantation, respectively (FIG. 5a). After 11 weeks post-transplantation the levels of $H2^b$ donor chimerism decreased in mice treated via IV-BMT or IL-BMT (p<0.05 versus 3 weeks). The chimeras presented lower levels of CD3$^+$ cells following IL-BMT, both at 3 and 11 weeks posttransplantation (p<0.05 versus IV-BMT, FIG. 5b).

Donor antigen-matched cardiac allografts (B10) transplanted 3 weeks following IV-BMT or IL-BMT were tolerated for periods exceeding 8 weeks, while third party grafts (B10.BR) were acutely rejected (Table 1).

TABLE 1

Allogeneic IL-BMT enables long-term tolerance of cardiac allografts.

| BMC donor | Route of BMC administration | Heart donor | Rejection time (days) | Mean survival time (days) |
|---|---|---|---|---|
| — | — | B10 | 8, 9 (×3), 10, 11 (×2) | 9.5 ± 1 |
| B10 | IV | B10 | >63 (×5) | >63* |
| B10 | IL | B10 | >56 (×5) | >56* |
| B10 | IL | B10.BR | 9 (×2), 10 (×3), 11 | 10 ± 1 |

B10 cardiac allografts were acutely rejected by naïve Balb/c recipients. Bone marrow transplantation was performed via IV-BMT and IL-BMT in non-myeloablated recipients (B10→Balb/c). Mean survival time of B10 secondary cardiac allografts transplanted three weeks following BMT was indicative of tolerance, while third-party (B10.BR) allografts were acutely rejected. Data represent mean ± standard deviation. *p < 0.05

These results therefore demonstrate that IL-BMT can be used to induce multilineage allogeneic donor specific hemopoietic chimerism and long-term tolerance of cardiac allografts in sublethally conditioned recipients.

IL-BMT or IB-BMT enables long-term tolerance of skin allografts in non-myeloablated recipients: The tolerogenic effect of IL-BMT was assessed by secondary transplantation of skin grafts, three weeks following BMT (B10→Balb/c) in recipients conditioned with 70 micrograms busulfan/g body weight. All recipients transplanted with $10^7$ whole BMCs via IV-BMT, IB-BMT and IL-BMT tolerated donor-matched skin grafts for periods exceeding 16 weeks (n=5). In a similar manner, skin grafts were accepted by all viable chimeras transplanted with T cell-depleted BMCs either via IV-BMT or IL-BMT (n=5). In variance, third party skin allografts (B10.BR) were acutely rejected in these experimental groups (n=3–4).

These results therefore demonstrate that IL-BMT can be used to enable long-term tolerance to skin allografts in non-myeloablated recipients.

IL-BMT enables long-term tolerance of skin allografts in recipients sublethally conditioned via local irradiation, regardless of low levels of donor PBL chimerism: Balb/c recipients conditioned by localized irradiation to the limb were administered $10^7$ whole BMCs from B10 donors via IL-BMT. At three weeks posttransplantation the levels of donor chimerism were low, in the range of 1% to 11% of donor PBLs (n=7). Secondary skin grafts (donor-matched) were accepted for periods exceeding 12 weeks. Additional measurements showed the same low levels of donor PBL chimerism throughout the follow-up period.

These results therefore demonstrate that IL-BMT enables long-term tolerance of skin allografts in recipients sublethally conditioned via local irradiation, regardless of low levels of donor PBL chimerism.

Simultaneous IL-BMT and skin grafting enables markedly higher levels of long-term skin allograft tolerance relative to simultaneous IV-BMT and skin grafting in non-myeloablated recipients: As described above, IL-BMT enables rapid BMC homing to and seeding in the recipient bone marrow, suggesting that IL-BMT may lead to rapid tolerance of allografts. In order to test this hypothesis, $10^7$ whole BMCs from B10 mice and donor-matched (n=7) or third party (B10.BR; n=3) skin allografts were simultaneously transplanted into Balb/c recipients subjected to non-myeloablative conditioning with 70 micrograms busulfan/g body weight. Mice treated with IL-BMT tolerated 71% (5/7) of B10 skin grafts for periods exceeding 8 weeks whereas, in marked contrast, mice treated with IV-BMT tolerated only 29% (2/7) of such skin grafts for such a time period. There was a slight delay in mean rejection time of both groups to 15±1.5 days (p<0.05 versus from 12±1 day without BMT). In both experimental groups third party (B10.BR) skin allografts were acutely rejected.

These results therefore demonstrate that simultaneous IL-BMT and skin grafting enables markedly higher levels of long-term skin allograft tolerance than simultaneous IV-BMT and skin grafting in non-myeloablated recipients.

Summary: These results demonstrate that IL-BMT using allogeneic BMCs performed according to the method of the present invention:

(i) in the short term results in higher levels of retention of administered donor derived BMCs in the bone marrow and in lower levels of systemic dissipation of administered donor derived BMCs relative to IB-BMT or IV-BMT;

(ii) restores hematopoiesis in lethally or supralethally conditioned recipients, with less graft-versus-host disease relative to IV-BMT in the case of the latter;

(iii) using whole or T cell depleted BMCs enables long-term donor specific PBL chimerism in non-myeloablated recipients;

(iv) enables generation of donor specific hemopoietic chimerism in sublethally conditioned recipients;

(v) using T cell depleted BMCs rescues lethally conditioned recipients;

(vi) enables long-term tolerance to cardiac allografts in sublethally conditioned recipients;

(vii) enables long-term tolerance to skin allografts in non-myeloablated recipients;

(viii) enables long-term tolerance to skin allografts in recipients sublethally conditioned via local irradiation, regardless of low levels of donor PBL chimerism; and (vii) performed simultaneously with skin grafting, enables long-term tolerance to skin allografts in non-myeloablated recipients.

Conclusion: The present invention enables: reconstitution of hematopoiesis in myeloablated animals; and establishment of tolerance to allogeneic BMC and organ grafts by transplantation of allogeneic BMCs, without the need for myeloablation or whole body irradiation and without the need for posttransplantation immunosuppression. As such, the present invention is clearly superior to all prior art methods of inducing immunological tolerance to allografts using BMC transplantation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. A method of inducing tolerance to a transplant transplanted from a donor to a subject, the method comprising:
    (a) administering myeloreduction or myeloablation treatment to the subject;
    (b) following step (a), restricting outflow of blood and/or lymph from a portion of the circulatory system of the subject; and (c) administering a dose of bone marrow cells derived from the donor to a body part delimiting said portion of the circulatory system, prior to, concomitantly with or following transplantation of the transplant, wherein said body part contains a bone marrow tissue, and wherein said restricting results in greater homing or retention of said dose of bone marrow cells in said bone marrow tissue relative to absence of said restricting, and does not cause ischemic injury to said bone marrow tissue, thereby inducing tolerance to the transplant in the subject.

2. The method of claim 1, wherein step (b) is effected prior to step (c).

3. The method of claim 1, wherein step (a) is effected by conditioning the subject under sublethal, lethal or supralethal conditions.

4. The method of claim 3, wherein step (a) is effected by administering a dose of irradiation essentially exclusively to a body part or a portion of said body part, wherein said body part or a portion of said body part contains a bone marrow tissue said body part or to a portion of said body part, said dose of irradiation being selected capable of inducing myeloreduction or myeloablation essentially exclusively in said body part or said portion of said body part.

5. The method of claim 3, wherein step (a) is effected by administering to the subject a dose of an agent selected from the group consisting of a myeloablative agent, a myeloreductive agent and an immunosuppressive agent.

6. The method of claim 5, wherein said myeloablative agent is busulfan.

7. The method of claim 6, wherein said dose of busulfan is less than or equal to a number of milligrams per kilogram body weight selected from a range of about 2 milligrams per kilogram body weight to about 20 milligrams per kilogram body weight.

8. The method of claim 1, wherein said restricting of said outflow of blood and/or lymph is effected using a method selected from the group consisting of applying at least one tourniquet to at least one margin of said body part, anastomosing said portion of the circulatory system to a perfusion apparatus so as to form an isolated circulatory system therewith, and ligating at least one vessel conducting said outflow of blood and/or lymph.

9. The method of claim 1, further comprising the step of restricting inflow of blood and/or lymph to said portion of the circulatory system.

10. The method of claim 9, wherein said restricting inflow of blood and/or lymph is effected prior to step (c).

11. The method of claim 9, wherein said restricting inflow of blood and/or lymph is effected using a method selected from the group consisting of applying at least one tourniquet to at least one margin of said body part, anastomosing said portion of the circulatory system to a perfusion apparatus so as to form an isolated circulatory system therewith, and ligating at least one vessel conducting said inflow of blood and/or lymph.

12. The method of claim 1, wherein said administering of said dose of bone marrow cells to said body part delimiting said portion of the circulatory system is effected by administering said dose of bone marrow cells to said portion of the circulatory system.

13. The method of claim 1, wherein the subject is human or murine.

14. The method of claim 1, wherein said dose of bone marrow cells is less than or equal to a number of cells per kilogram body weight selected from a range of about one million cells per kilogram body weight to about 2 billion cells per kilogram body weight.

15. The method of claim 1, wherein said dose of bone marrow cells is selected from the group consisting of a dose of whole bone marrow cells, a dose of mobilized peripheral blood cells, a dose of umbilical cord blood cells, a dose of T-cell depleted bone marrow cells, a dose of T-cell depleted mobilized peripheral blood cells and a dose of T-cell depleted umbilical cord blood cells.

16. The method of claim 1, wherein said dose of bone marrow cells is selected from the group consisting of a dose of erythrocyte depleted bone marrow cells, a dose of erythrocyte depleted stem cells and a dose of erythrocyte depleted progenitor cells.

17. The method of claim 1, wherein said dose of bone marrow cells is selected from the group consisting of a dose of nucleated bone marrow cells, a dose of nucleated mobilized peripheral blood cells and a dose of nucleated umbilical cord blood cells.

18. The method of claim 1, wherein the donor and the subject are allogeneic or syngeneic, and/or wherein the donor is the subject.

19. The method of claim 1, wherein said body part is a limb or a portion thereof.

20. The method of claim 19, wherein said limb is a leg.

21. The method of claim 1, wherein the transplant is selected from the group consisting of an organ transplant, a tissue transplant and a cell transplant.

22. The method of claim 21, wherein said organ transplant is selected from the group consisting of a cardiac transplant, a liver transplant, a kidney transplant, a pancreatic islet transplant and a beta-cell transplant.

23. The method of claim 21, wherein said tissue transplant is selected from the group consisting of a skin transplant, a bone transplant, a cartilage transplant and a muscle transplant.

24. The method of claim 21, wherein said cell transplant is selected from the group consisting of a bone marrow cell transplant, a mobilized peripheral blood cell transplant and an umbilical cord blood cell transplant.

25. The method of claim 21, wherein said cell transplant is said dose of bone marrow cells.

26. A method of transplanting a transplant from a donor to a subject, the method comprising:
(a) administering myeloreduction or myeloablation treatment to the subject;
(b) following step (a), restricting outflow of blood and/or lymph from a portion of the circulatory system of the subject;
(c) administering a dose of bone marrow cells derived from the donor to a body part delimiting said portion of the circulatory system, wherein said body part contains a bone marrow tissue, and wherein said restricting results in greater homing or retention of said dose of bone marrow cells in said bone marrow tissue relative to absence of said restricting, and does not cause ischemic injury to said bone marrow tissue; and
(d) transplanting the transplant from the donor to the subject prior to, concomitantly with or following step (c).

27. The method of claim 26, wherein step (a) is effected by conditioning the subject under sublethal, lethal or supralethal conditions.

28. The method of claim 27, wherein said step (a) is effected by administering a dose of irradiation essentially exclusively to a body part or a portion of said body part, wherein said body part or a portion of said body part contains a bone marrow tissue said body part or to a portion of said body part, said dose of irradiation being selected capable of inducing myeloreduction or myeloablation essentially exclusively in said body part or said portion of said body part.

29. The method of claim 27, wherein step (a) is effected by administering to the subject a dose of an agent selected from the group consisting of a myeloablative agent, a myeloreductive agent and an immunosuppressive agent.

30. The method of claim 29, wherein said myeloablative agent is busulfan.

31. The method of claim 30, wherein said dose of busulfan is less than or equal to a number of milligrams per kilogram body weight selected from a range of about 2 milligrams per kilogram body weight to about 20 milligrams per kilogram body weight.

32. The method of claim 26, wherein said restricting outflow of blood and/or lymph is effected using a method selected from the group consisting of applying at least one tourniquet to at least one margin of said body part, adjoining said portion of the circulatoty system to a perfusion apparatus so as to form an isolated circulatory system therewith, and ligating at least one vessel conducting said outflow of blood and/or lymph.

33. The method of claim 26, further comprising the step of restricting inflow of blood and/or lymph to said portion of the circulatory system.

34. The method of claim 33, wherein said restricting inflow of said blood and/or lymph is effected prior to step (c).

35. The method of claim 33, wherein said restricting inflow of blood and/or lymph is effected using a method selected from the group consisting of applying at least one tourniquet to at least one margin of said body part, anastomosing said portion of the circulatory system to a perfusion apparatus so as to form an isolated circulatory system therewith, and ligating at least one vessel conducting said inflow of blood and/or lymph.

36. The method of claim 26, wherein said administering of said dose of bone marrow cells to said body part delimiting said portion of the circulatory system is effected by administering said dose of bone marrow cells to said portion of the circulatory system.

37. The method of claim 26, wherein the subject is human or murine.

38. The method of claim 26, wherein said dose of bone marrow cells is less than or equal to a number of cells per kilogram body weight selected from a range of about one million cells per kilogram body weight to about 2 billion cells per kilogram body weight.

39. The method of claim 26, wherein said dose of bone marrow cells is selected from the group consisting of a dose of whole bone marrow cells, a dose of mobilized peripheral blood cells, a dose of umbilical cord blood cells, a dose of T-cell depleted bone marrow cells, a dose of T-cell depleted mobilized peripheral blood cells and a dose of T-cell depleted umbilical cord blood cells.

40. The method of claim 26, wherein said dose of bone marrow cells is selected from the group consisting of a dose of erythrocyte depleted bone marrow cells, a dose of erythrocyte depleted stem cells and a dose of erythrocyte depleted progenitor cells.

41. The method of claim 26, wherein said dose of bone marrow cells is selected from the group consisting of a dose of nucleated bone marrow cells, a dose of nucleated mobilized peripheral blood cells and a dose of nucleated umbilical cord blood cells.

42. The method of claim 26, wherein the donor and the subject are allogeneic or syngeneic, and/or wherein the donor is the subject.

43. The method of claim 26, wherein said body part is a limb or a portion thereof.

44. The method of claim 43, wherein said limb is a leg.

45. The method of claim 26, wherein the transplant is selected from the group consisting of an organ transplant, a tissue transplant and a cell transplant.

46. The method of claim 45, wherein said organ transplant is selected from the group consisting of a cardiac transplant, a liver transplant, a kidney transplant, a pancreatic islet transplant and a beta-cell transplant.

47. The method of claim 45, wherein said tissue transplant is selected from the group consisting of a skin transplant, a bone transplant, a cartilage transplant and a muscle transplant.

48. The method of claim 45, wherein said cell transplant is selected from the group consisting of a bone marrow cell transplants, a mobilized peripheral blood cell transplant and an umbilical cord blood cell transplant.

49. The method of claim 45, wherein said cell transplant is said dose of bone marrow cells.

* * * * *